(12) United States Patent
Metzger et al.

(10) Patent No.: US 8,894,715 B2
(45) Date of Patent: Nov. 25, 2014

(54) KNEE PROSTHESIS

(75) Inventors: Robert Metzger, Wakarusa, IN (US); James G. Lancaster, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 0 days.

(21) Appl. No.: 13/609,389

(22) Filed: Sep. 11, 2012

(65) Prior Publication Data
US 2013/0006375 A1    Jan. 3, 2013

Related U.S. Application Data

(63) Continuation-in-part of application No. 12/788,961, filed on May 27, 2010, now abandoned.

(60) Provisional application No. 61/181,938, filed on May 28, 2009.

(51) Int. Cl.
*A61F 2/38* (2006.01)
*A61F 2/30* (2006.01)

(52) U.S. Cl.
CPC ..... *A61F 2/3868* (2013.01); *A61F 2002/30604* (2013.01); *A61F 2002/30462* (2013.01); *A61F 2002/30884* (2013.01); *A61F 2/38* (2013.01); *A61F 2002/3895* (2013.01); *A61F 2220/0075* (2013.01); *A61F 2002/30387* (2013.01); *A61F 2002/30481* (2013.01); *A61F 2002/30405* (2013.01); *A61F 2002/30892* (2013.01)
USPC ............... 623/20.31; 623/20.15; 623/20.28

(58) Field of Classification Search
USPC .......... 623/20.14, 20.15, 20.19, 20.21, 20.28, 623/20.31, 20.32, 20.34, 20.35
See application file for complete search history.

(56) References Cited

U.S. PATENT DOCUMENTS

| 4,207,627 A | 6/1980 | Cloutier |
| 4,711,639 A | 12/1987 | Grundei |
| 4,728,332 A | 3/1988 | Albrektsson |

(Continued)

FOREIGN PATENT DOCUMENTS

| EP | 0447065 A2 | 9/1991 |
| EP | 0552950 A1 | 7/1993 |
| EP | 1741412 A2 | 1/2007 |

OTHER PUBLICATIONS

International Search Report for International Application No. PCT/US2010/036602 dated Nov. 8, 2010.

(Continued)

*Primary Examiner* — Marcia Watkins
(74) *Attorney, Agent, or Firm* — Harness, Dickey

(57) ABSTRACT

A knee joint prosthesis assembly according to the present disclosure can include a femoral component, a unitary tibial component, a medial bearing, and a lateral bearing. The femoral component can have a medial and a lateral condyle portion connected by a patellar track portion. The femoral component can form an opening between the medial and lateral condyles. The unitary tibial component can have a medial portion that includes a first posterior engagement lip and a first outer securing lip. The tibial component can further include a lateral portion that includes a second posterior engagement lip and a second outer securing lip. The medial bearing can have a first posterior groove formed thereon that selectively engages the first posterior engagement lip and a first outer groove that selectively engages the first outer securing lip.

17 Claims, 20 Drawing Sheets

(56) References Cited

U.S. PATENT DOCUMENTS

| | | | |
|---|---|---|---|
| 4,795,468 A | 1/1989 | Hodorek et al. | |
| 5,080,675 A * | 1/1992 | Lawes et al. | 623/20.33 |
| 5,282,868 A | 2/1994 | Bahler | |
| 5,330,534 A | 7/1994 | Herrington et al. | |
| 5,344,460 A * | 9/1994 | Turanyi et al. | 623/20.33 |
| 5,358,530 A | 10/1994 | Hodorek | |
| 5,358,531 A | 10/1994 | Goodfellow et al. | |
| 5,395,401 A | 3/1995 | Bahler | |
| 5,470,354 A | 11/1995 | Hershberger et al. | |
| 5,480,446 A | 1/1996 | Goodfellow et al. | |
| 5,702,464 A * | 12/1997 | Lackey et al. | 623/20.32 |
| 5,871,542 A | 2/1999 | Goodfellow et al. | |
| 5,871,543 A | 2/1999 | Hofmann | |
| 5,928,286 A | 7/1999 | Ashby et al. | |
| 5,964,808 A | 10/1999 | Blaha et al. | |
| 5,968,099 A | 10/1999 | Badorf et al. | |
| 6,013,103 A | 1/2000 | Kaufman et al. | |
| 6,190,415 B1 | 2/2001 | Cooke et al. | |
| 6,210,445 B1 | 4/2001 | Zawadzki | |
| 6,500,208 B1 | 12/2002 | Metzger et al. | |
| 6,923,832 B1 | 8/2005 | Sharkey et al. | |
| 6,946,001 B2 | 9/2005 | Sanford et al. | |
| 7,033,397 B2 | 4/2006 | Webster et al. | |
| 7,060,101 B2 | 6/2006 | O'Connor et al. | |
| 7,105,026 B2 * | 9/2006 | Johnson et al. | 623/20.14 |
| 7,255,715 B2 | 8/2007 | Metzger | |
| 7,354,354 B2 | 4/2008 | Palumbo et al. | |
| 7,462,198 B2 | 12/2008 | Webster et al. | |
| 7,463,198 B2 | 12/2008 | Deaett et al. | |
| 8,066,776 B2 | 11/2011 | O'Connor et al. | |
| 8,075,626 B2 | 12/2011 | Dun | |
| 8,137,407 B2 | 3/2012 | Todd et al. | |
| 8,142,510 B2 | 3/2012 | Lee et al. | |
| 8,147,557 B2 | 4/2012 | Lee et al. | |
| 8,147,558 B2 | 4/2012 | Lee et al. | |
| 2003/0093156 A1 * | 5/2003 | Metzger et al. | 623/20.15 |
| 2003/0187510 A1 | 10/2003 | Hyde | |
| 2005/0154471 A1 * | 7/2005 | Aram et al. | 623/20.15 |
| 2005/0209703 A1 | 9/2005 | Fell | |
| 2006/0004460 A1 | 1/2006 | Engh et al. | |
| 2007/0078517 A1 | 4/2007 | Engh et al. | |
| 2008/0243260 A1 * | 10/2008 | Lee et al. | 623/20.33 |
| 2008/0243261 A1 | 10/2008 | Wyss et al. | |
| 2008/0243262 A1 | 10/2008 | Lee | |
| 2008/0257363 A1 | 10/2008 | Schoenefeld et al. | |
| 2010/0305698 A1 | 12/2010 | Metzger et al. | |
| 2010/0305709 A1 | 12/2010 | Metzger et al. | |
| 2010/0305710 A1 | 12/2010 | Metzger et al. | |
| 2011/0040387 A1 | 2/2011 | Ries et al. | |
| 2012/0239159 A1 | 9/2012 | Metzger et al. | |

OTHER PUBLICATIONS

Written Opinion of the International Searching Authority for International Application No. PCT/US2010/06602 dated May 28, 2010.
International Preliminary Examination Report for International Application No. PCT/US2010/036602 dated May 28, 2010.
International Search Report and Written Opinion for PCT/US2013/058921 mailed Oct. 21, 2013 claiming benefit of U.S. Appl. No. 13/609,389, filed Sep. 11, 2012.

* cited by examiner

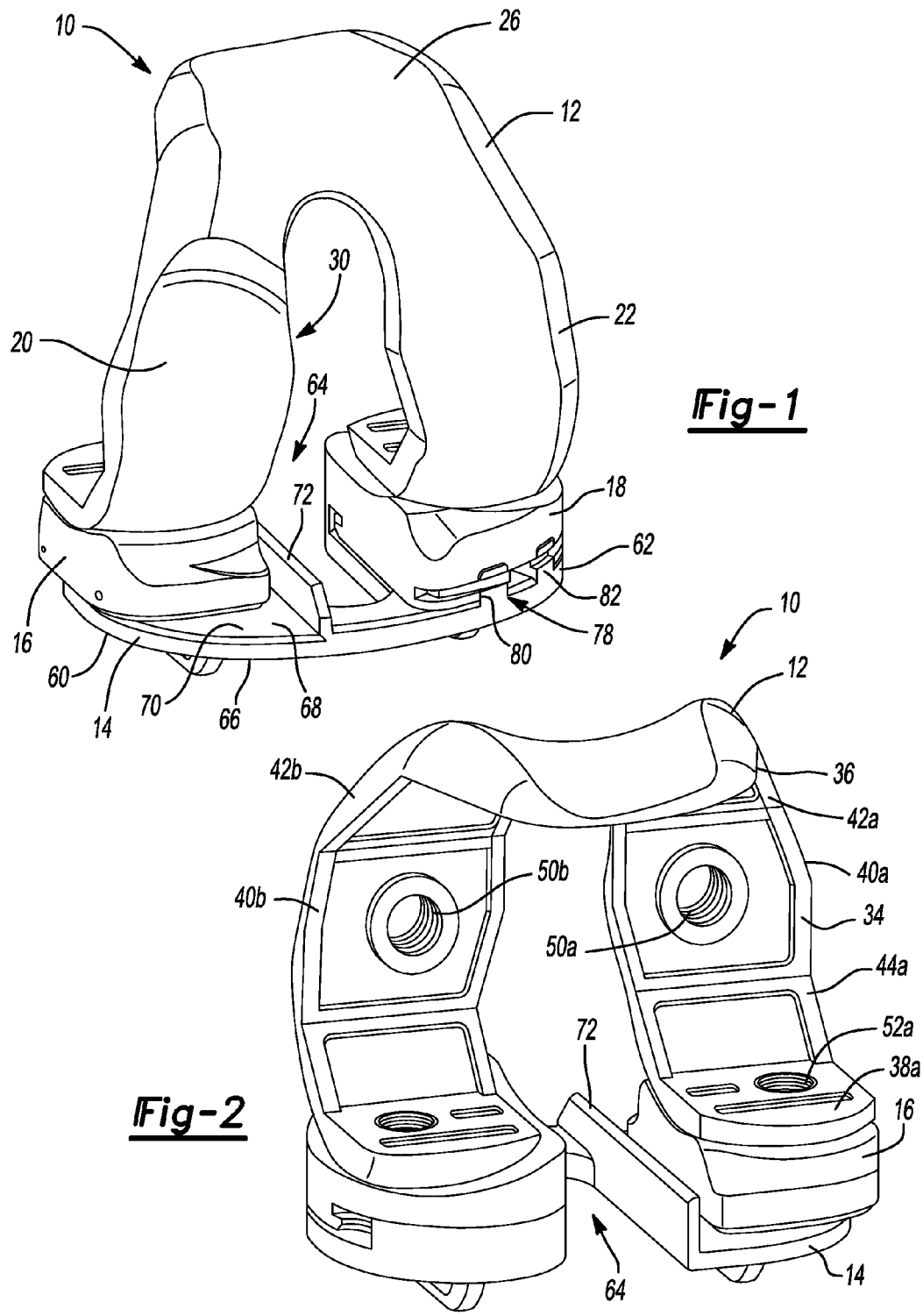

KNEE PROSTHESIS

CROSS-REFERENCE TO RELATED APPLICATIONS

This application is a continuation-in-part of U.S. patent application Ser. No. 12/788,961 filed on May 27, 2012, which claims the benefit and priority of U.S. Patent Application No. 61/181,938 filed May 28, 2009. The entire disclosure of the above applications is incorporated herein by reference.

FIELD

The present disclosure relates to a knee joint prosthesis including a tibial tray component having independent and selectively attachable bearings including fixed and mobile bearings that can be secured to medial and lateral sides of the tibial tray according to the needs of a particular patient.

BACKGROUND

This section provides background information related to the present disclosure which is not necessarily prior art.

A knee joint prosthesis can generally comprise a femoral component and a tibial component. The femoral component and the tibial component can be designed to be surgically attached to the distal end of the femur and the proximal end of the tibia, respectively. The femoral component can further be designed to cooperate with the tibial component in simulating the articulating motion of an anatomical knee joint. In many examples, the tibial component can further include a bearing component that includes articulation surfaces on the medial and lateral side for cooperating with a medial and lateral condyle portion of the femoral component. In some examples, the bearing component can be fixed relative to the tibial component. In other examples, the bearing component can be a mobile bearing component that has at least a portion that can move relative to the tibial component during articulation of the femoral component.

SUMMARY

This section provides a general summary of the disclosure, and is not a comprehensive disclosure of its full scope or all of its features.

A knee joint prosthesis assembly according to the present disclosure can include a femoral component, a unitary tibial component, a medial bearing, and a lateral bearing. The femoral component can have a medial and a lateral condyle portion connected by a patellar track portion. The femoral component can form an opening between the medial and lateral condyles. The unitary tibial component can have a medial portion that includes a first posterior engagement lip and a first outer securing lip. The tibial component can further include a lateral portion that includes a second posterior engagement lip and a second outer securing lip. The medial bearing can have a first posterior groove formed thereon that selectively engages the first posterior engagement lip and a first outer groove that selectively engages the first outer securing lip. The lateral bearing can be separately formed and independent from the medial bearing. The lateral bearing can have a second posterior groove formed thereon that selectively engages the second posterior engagement lip and a second outer groove formed thereon that selectively engages the second outer securing lip.

The tibial component can further comprise a first peg that extends inferiorly from the medial portion and a second peg extending inferiorly from the lateral portion. The tibial component can further comprise a first keel extending inferiorly from the medial portion and a second keel extending inferiorly from the lateral portion. The medial and lateral condyles of the femoral component can be configured to articulate along complementary bearing surfaces of the medial and lateral bearings. The medial and lateral bearings can both be configured to be fixed relative to the tibial component.

According to additional features, a locking bar can selectively locate between the tibial component and the medial and lateral bearings. The locking bar can secure the medial and lateral bearings to the tibial component. The tibial component can be U-shaped and be adapted to accommodate an anterior cruciate ligament. The tibial component can have an inferiorly extending stem. According to other features, the knee joint prosthesis can further comprise a plurality of separate fixed medial and lateral bearings. The plurality of medial and lateral bearings can have distinct thicknesses in a superior/inferior direction.

A knee joint prosthesis assembly constructed in accordance to the present disclosure can include a femoral component having a medial and a lateral condyle portion connected by a patellar track portion. The femoral component can form an opening between the medial and lateral condyles. The knee joint prosthesis assembly can further include a unitary tibial component, a medial bearing and a lateral bearing. The unitary tibial component can have a medial portion that includes a first pair of distinct and spaced apart engagement lips and a lateral portion that includes a second pair of distinct and spaced apart engagement lips. The medial bearing can have a first pair of distinct and spaced apart grooves formed thereon that selectively engage the first pair of engagement lips. The lateral bearing can be separately formed and independent from the medial bearing and have a second pair of distinct and spaced apart grooves formed thereon that selectively engage the second pair of engagement lips.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an anterior perspective view of a knee prosthesis assembly according to one example of the present teachings;

FIG. 2 is a posterior perspective view of the knee prosthesis of FIG. 1;

Corresponding reference numerals indicate corresponding parts throughout the several views of the drawings.

DETAILED DESCRIPTION

Figure 3:
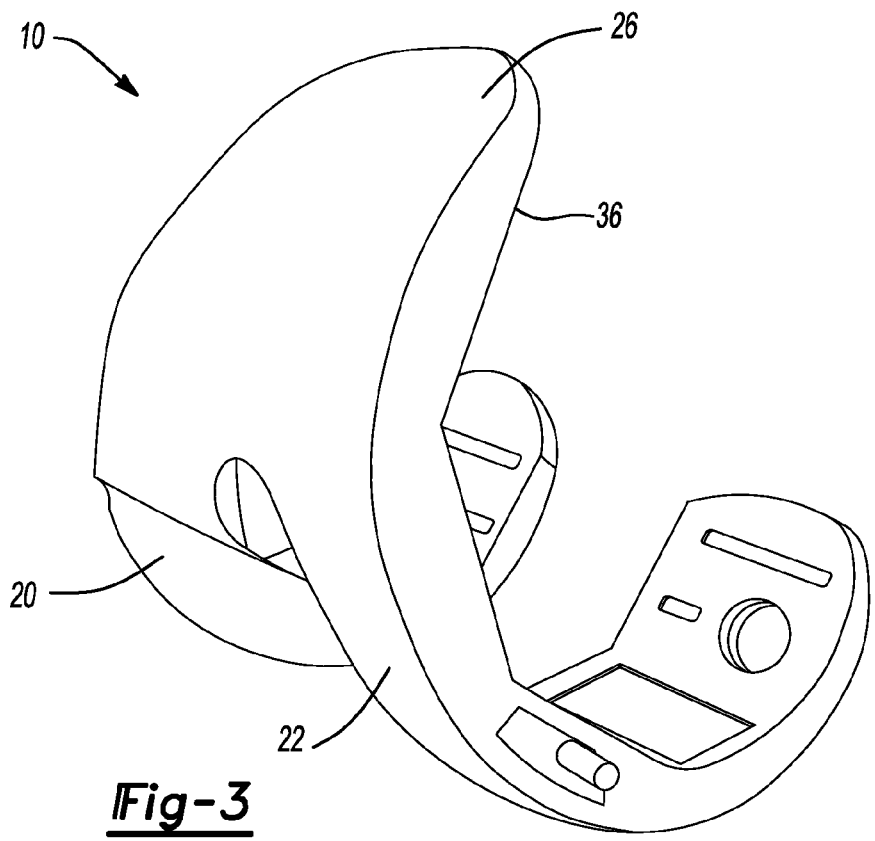
FIG. 3 is a lateral perspective view of a femoral component of the knee prosthesis of FIG. 1.

Example embodiments will now be described more fully with reference to the accompanying drawings.

With initial reference to FIGS. 1 and 2, a knee prosthesis assembly constructed in accordance to one example of the present teachings is shown and generally identified at reference numeral 10. The knee prosthesis assembly 10 can generally include a femoral component 12, a tibial tray 14, a medial floating or mobile bearing 16 and a lateral fixed bearing 18. As will be described, the knee prosthesis assembly 10 can be used when it is desirable to retain or reconstruct an anterior cruciate ligament (ACL) and/or a posterior cruciate ligament (PCL).

The respective components of the knee prosthesis assembly 10 can be patient specific, such that each component can be constructed for optimal features for a given patient. For example, the bone interface margins of the femoral component 12 and tibial tray 14 can be patient specific for optimized bone coverage. In addition, the overall size, such as anterior-posterior dimensions and bone cut geometry can be determined and used for manufacturing the components of the knee prosthesis assembly 10. Moreover, some articulation features can be determined and used as criteria for forming the components of the knee prosthesis assembly 10. In sum, each of the components of the knee prosthesis assembly 10 can be a patient-specific implant, a semi-custom implant or an off-the-shelf or standard production implant. A custom-made implant is a patient-specific, one-of-a-kind implant specifically made for a particular patient, and consequently there is no inventory associated with such implant. Standard or off-the shelf implants are available and stocked in a number of sizes, typically six or more, and a number of configurations or types, including bilateral or unilateral implants, constrained, semi-constrained, mobile, etc. Because of the variety of sizes and configurations that are kept in stock to be accommodated by different patients, a large inventory of standard implants is created, and several molds for each type and size of implant may be used. Semi-custom implants can provide an intermediate solution between custom-made and off-the-shelf implants. Semi-custom implants reduce the size of inventory and molds required for production, while allowing some degree of patient-specific customization. Additional description of patient-specific implants and semi-custom implants and their implementations may be found in copending patent application Ser. No. 12/103,824, filed Apr. 16, 2008 and entitled: Method and Apparatus for Manufacturing an Implant, the disclosure of which is hereby incorporated by reference.

With additional reference to FIG. 3, the femoral component 12 will now be described in greater detail. The femoral component 12 can generally comprise a cruciate retaining prosthesis and includes various portions to replace or mimic the distal femur. The femoral component 12 can include a medial condyle portion 20 and a lateral condyle portion 22. The condyle portions 20 and 22 can replace the medial and lateral condyles of a distal femur. The medial and lateral condyle portions 20 and 22 can interconnect and be formed as a single piece with a patellar track portion 26. The patellar track portion 26 can allow for articulation of a patella, either natural or prosthetic patella, once the femoral component 12 is implanted onto the distal femur. The medial and lateral condyle portions 20 and 22 and the patellar track portion 26 can generally define an exterior portion of the femoral component 12. The femoral component 12 can define an opening or passage 30 between the medial and lateral condyle portions 20 and 22. As can be appreciated, the passage 30 can accommodate, and provide clearance for a host ACL and/or PCL or a reconstructed ACL and/or PCL. The medial condyle portion 20 can include a spherical contact surface that is convex in an anterior/posterior direction and a medial/lateral direction.

The femoral component 12 can include a bone contacting or inferior surface 34 (FIG. 2). The inferior surface 34 can include an anterior surface 36 that can be substantially flat and formed generally parallel to a pair of posterior surfaces 38a and 38b. A pair of intermediate surfaces 40a and 40b are provided generally at an intermediate portion of the inferior surface 34. A pair of angled anterior transition surfaces 42a and 42b generally connect the anterior surface 36 with the intermediate surfaces 40a and 40b. Similarly, a pair of angled posterior transition surfaces 44a and 44b are provided between the respective posterior surfaces 38a and 38b and the intermediate surfaces 40a and 40b. In one example, a threaded boss 50a and 50b can be provided on each of the intermediate surfaces 40a and 40b, respectively. Similarly, a threaded boss 52a and 52b can be provided on the posterior surfaces 38a and 38b, respectively. The bosses 50a, 50b, 52a and 52b can be optionally used to threadably couple with various augments (not specifically shown) as necessary. The femoral component 12 can be formed as a unitary structure and cast of a biocompatible high strength alloy, such as cobalt-chromium-molybdenum alloy or similar suitable material. All surfaces, which do not contact the femur, can be highly polished to provide smooth articulating bearing surfaces. The interior surface 34 of the femoral component 12 can be roughened or uneven or include porous material to allow bone ingrowth or attachment with bone cement. Other features of the femoral component 12 can include those associated with the Oxford® Partial Knee marketed by Biomet, Inc.

Figure 4:
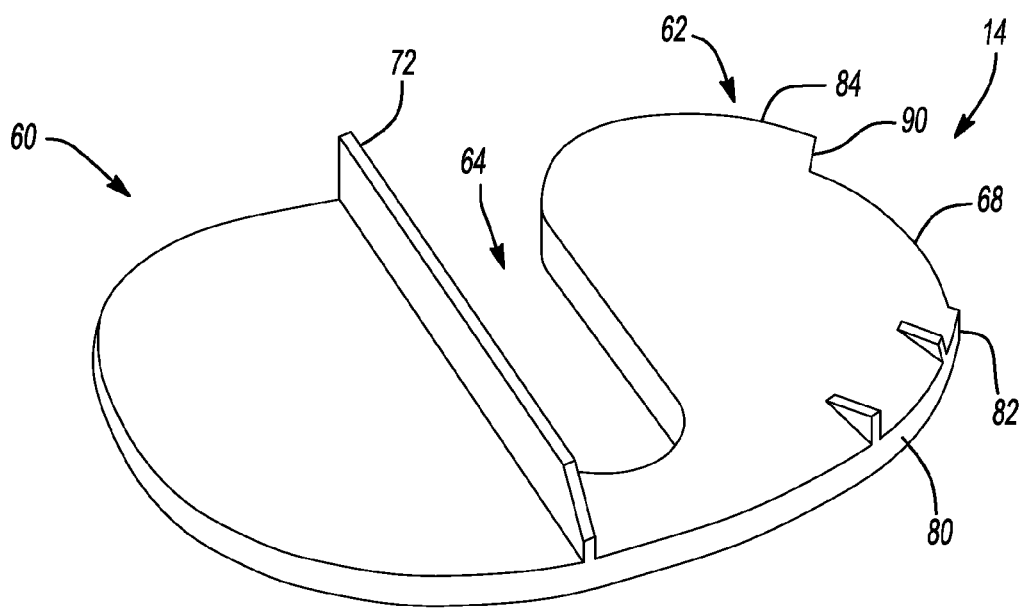
FIG. 4 is a superior perspective view of a tibial tray of the knee prosthesis of FIG. 1.
Figure 5:
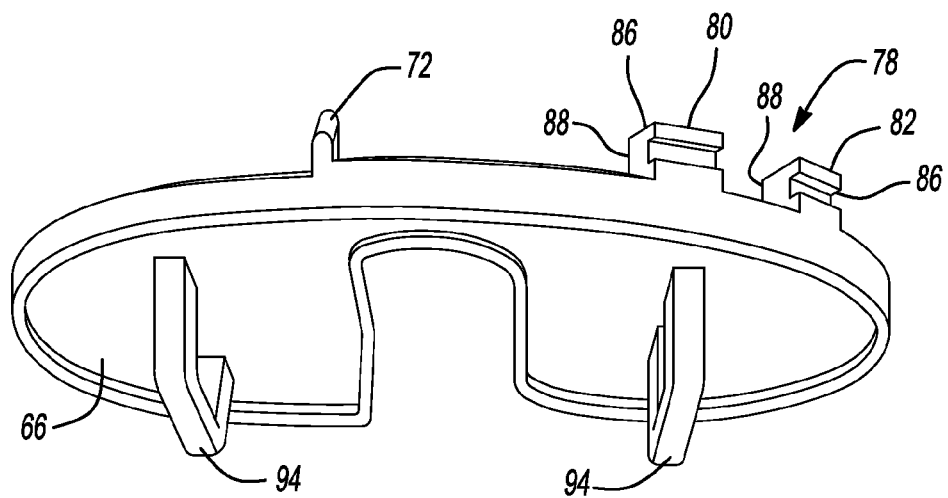
FIG. 5 is an inferior perspective view of the tibial tray of FIG. 4.

With reference now to FIGS. 1, 2, 4 and 5, the tibial tray 14 will now be described in greater detail. The tibial tray 14 can include a generally U-shaped body having a medial portion 60 and a lateral portion 62. A slot 64 can be formed in the tibial tray 14 generally between the medial and lateral portion 60 and 62. As with the passage 30 of the femoral component, the slot 64 of the tibial tray 14 can accommodate and provide a clearance for a host ACL and/or PCL or a reconstructed ACL and/or PCL. During implantation, the tibial tray 14 can be advanced posteriorly, such that the slot 64 can accommodate a host ACL and/or PCL. In instances where a reconstructed ACL and/or PCL is used, a tray (and bearing) having a passage can be utilized. One suitable configuration is further described in commonly owned in U.S. Pat. No. 7,255,715; issued Aug. 14, 2007 and is hereby incorporated by reference. The tibial tray 14 can include an inferior bone engaging side 66 (FIG. 5) and a superior bearing engaging side 68 (FIG. 4). The medial portion 60 of the superior bearing engaging side 68 can include a highly polished tibial bearing surface 70. A rail 72 can extend in a generally anterior/posterior direction adjacent to the highly polished tibial bearing surface 70. The lateral portion 62 can include engaging structure 78 provided on the superior bearing engaging side 68. The engaging structure 78 can include a pair of posts 80 and 82 integrally formed at an anterior edge thereof. A retaining rail 84 can extend superiorly from a posterior edge of the lateral portion 62. The posts 80 and 82 can both have an anterior groove 86 and a posterior groove 88, respectively. The retaining rail 84 can have a transverse groove 90 formed on an inwardly facing surface. The tibial tray 14 can be generally manufactured of cobalt-chromium-molybdenum alloy or other suitable biocompatible material. A pair of fins 94 can extend from the inferior bone engaging side 66. While fins 94 are shown operatively associated with the tibial tray 14, other structures suitable for engaging a proximal tibia can include pegs, posts or porous material can additionally or alternatively be provided on the inferior bone engaging side 66.

Figure 6:
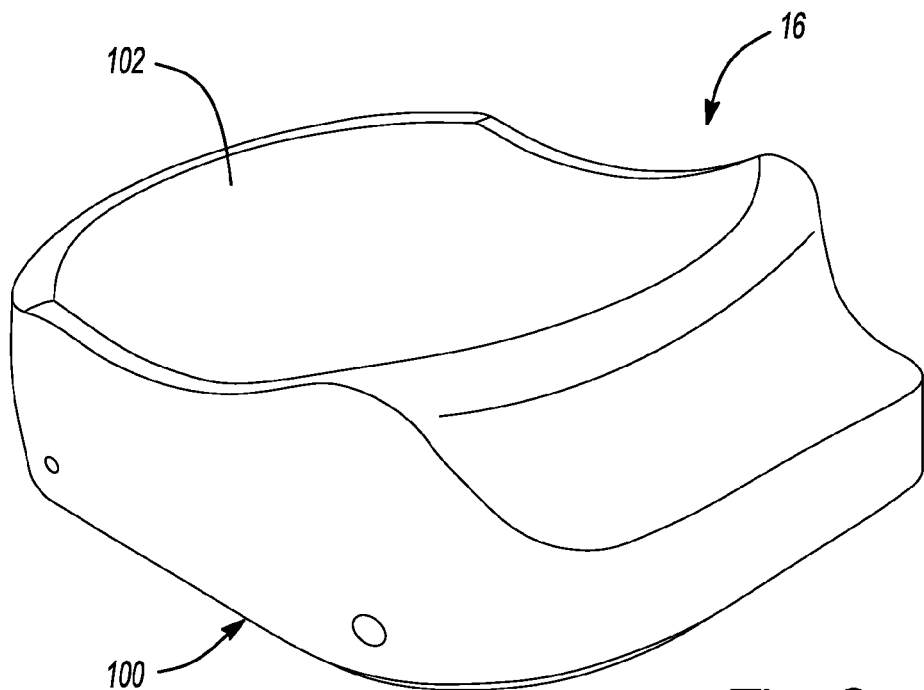
FIG. 6 is a perspective view of a mobile bearing of the knee prosthesis of FIG. 1.

With reference to FIGS. 1, 2 and 6, the medial floating bearing 16 will now be described in greater detail. The medial floating bearing 16 has a substantially planar inferior bearing surface 100 which slidably moves and articulates relative to the highly polished tibial bearing surface 70. The medial floating bearing 16 further includes a first bearing surface 102. The first bearing surface 102 articulates with the medial condyle portion 20 of the femoral component 12. The medial floating bearing 16 can be formed from a surgical grade, low friction, and low wearing plastic, such as ultra high molecular weight polyethylene (UHMWPE) or other suitable material.

Figure 7:
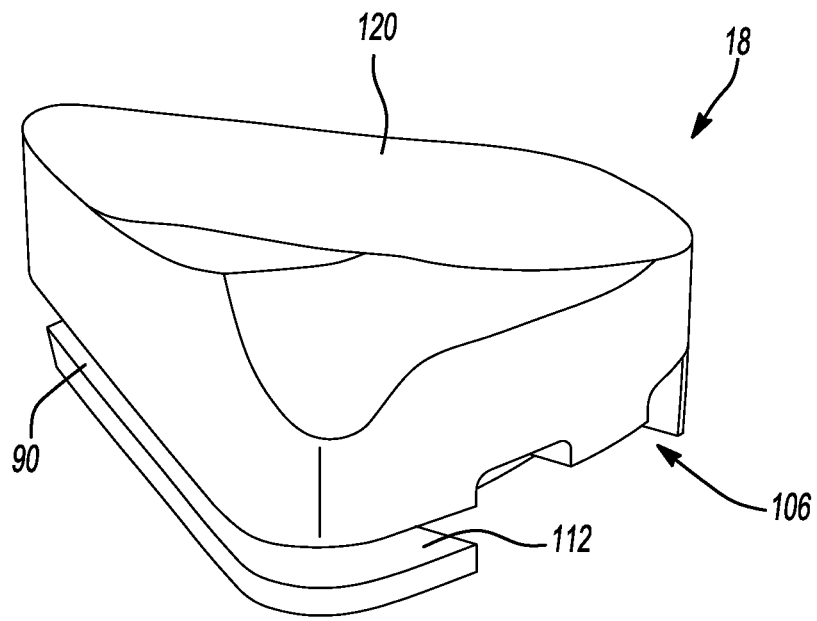
FIG. 7 is a perspective view of a fixed bearing of the knee prosthesis of FIG. 1.
Figure 8:
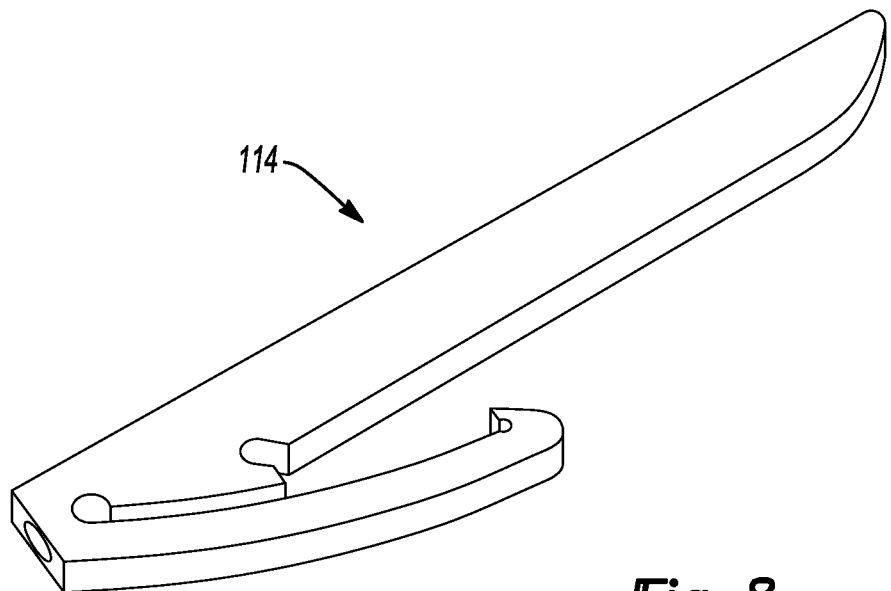
FIG. 8 is a perspective view of a locking bar associated with the fixed bearing of a knee prosthesis of FIG. 1.

With reference to FIGS. 1, 2 and 7, the lateral fixed bearing 18 can include engaging structure 106 formed on an inferior surface for coupling with the engaging structure 78 provided on the lateral portion 62 of the tibial tray 14. The engaging structure 106 can generally include a posteriorly extending lip 110 and an anterior groove 112. A locking bar 114 (FIG. 8) can be slidably inserted through the anterior groove 112 to interlock between the respective grooves 86 to capture the lateral fixed bearing 18 to the lateral portion 62 of the tibial tray 14. The posteriorly extending lip 110 can be nestingly received by the retaining rail 84. The lateral fixed bearing 18 can include a second bearing surface 120. The second bearing surface 120 can articulate with the lateral condyle portion 22 of the femoral component 12. The lateral fixed bearing 18 can be formed from a surgical grade, low friction and low wearing plastic, such as UHMWPE or other suitable material.

During use, the medial and lateral condyle portions 20 and 22 of the femoral component 12 can articulate on the first and second bearing surfaces 102 and 120 of the respective medial floating bearing 16 and lateral fixed bearing 18. As can be appreciated, the lateral fixed bearing 18 is static relative to the tibial tray 14 during articulation of the femoral component 12. The medial floating bearing 16 is free to slide along the highly polished tibial bearing surface 70 of the medial portion 60 of the tibial tray 14. The medial floating bearing 16 is bound on an inboard side by the rail 72.

Figure 9:
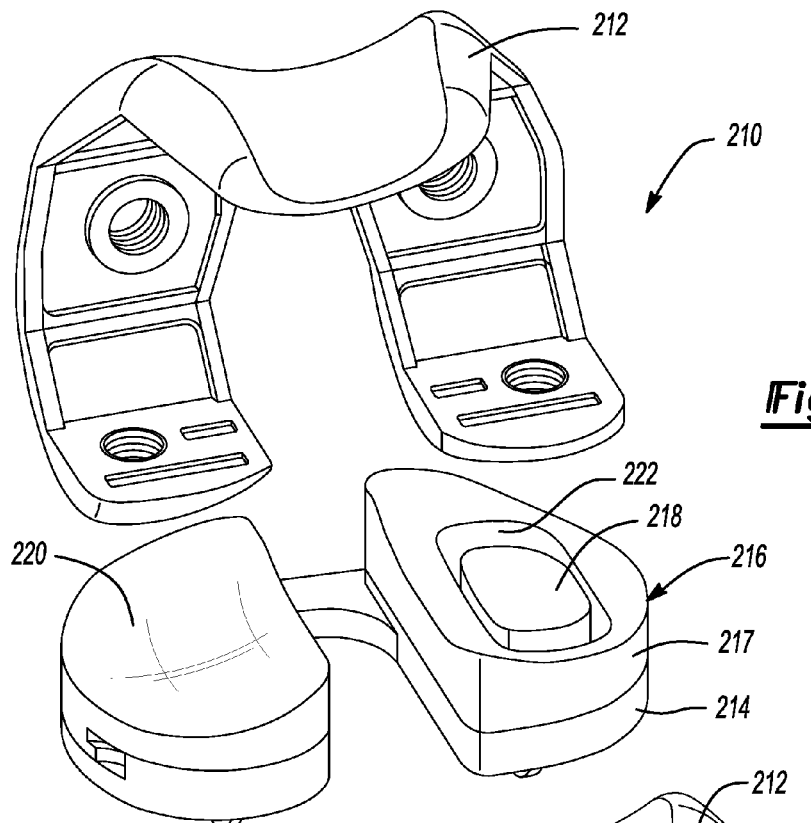
FIG. 9 is a partially exploded posterior view of a knee prosthesis constructed in accordance to additional features of the present teachings.
Figure 10:
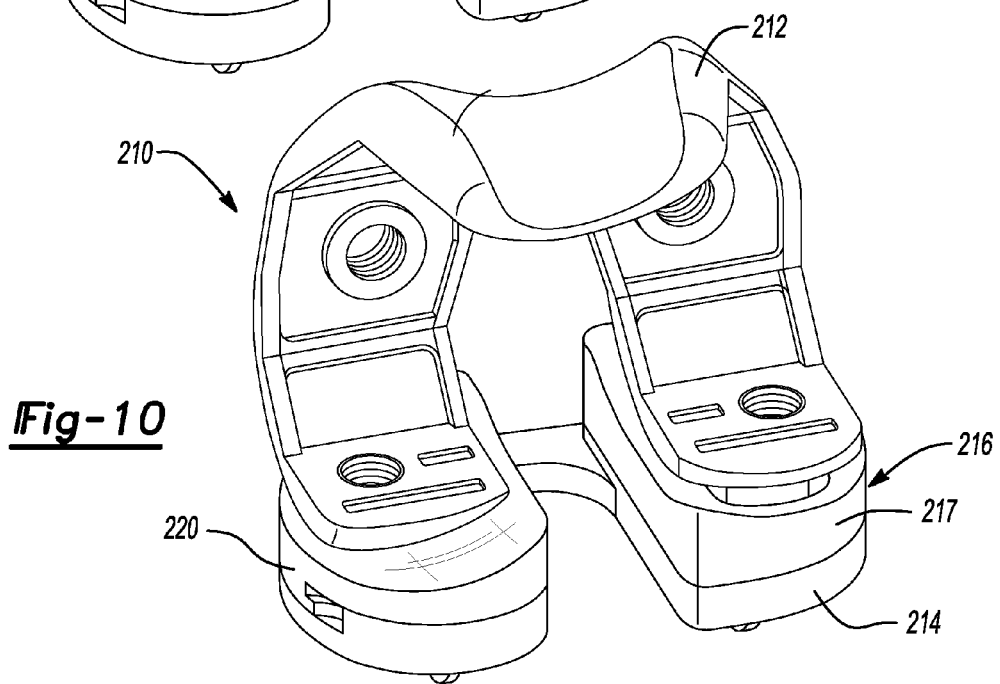
FIG. 10 is a posterior perspective view of the knee prosthesis of FIG. 9.
Figure 11:
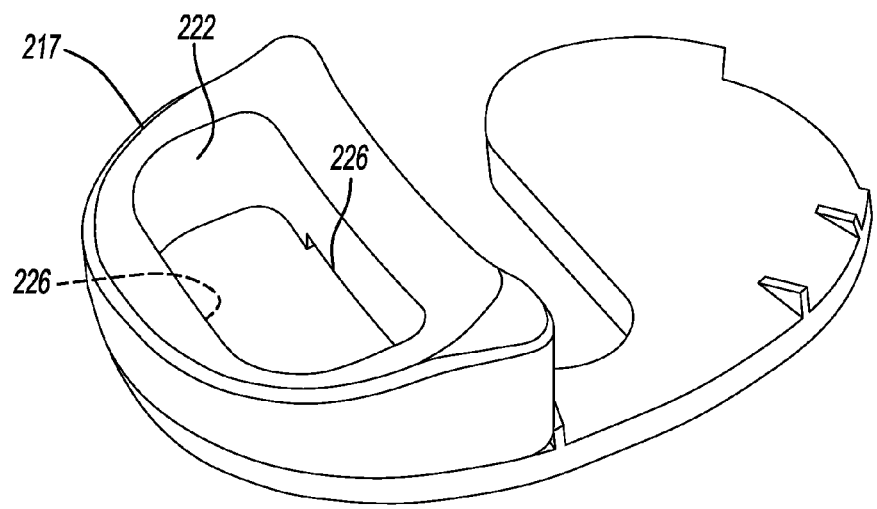
FIG. 11 is an anterior perspective view of a tibial tray and fixed bearing portion of the knee prosthesis of FIG. 10.
Figure 12:
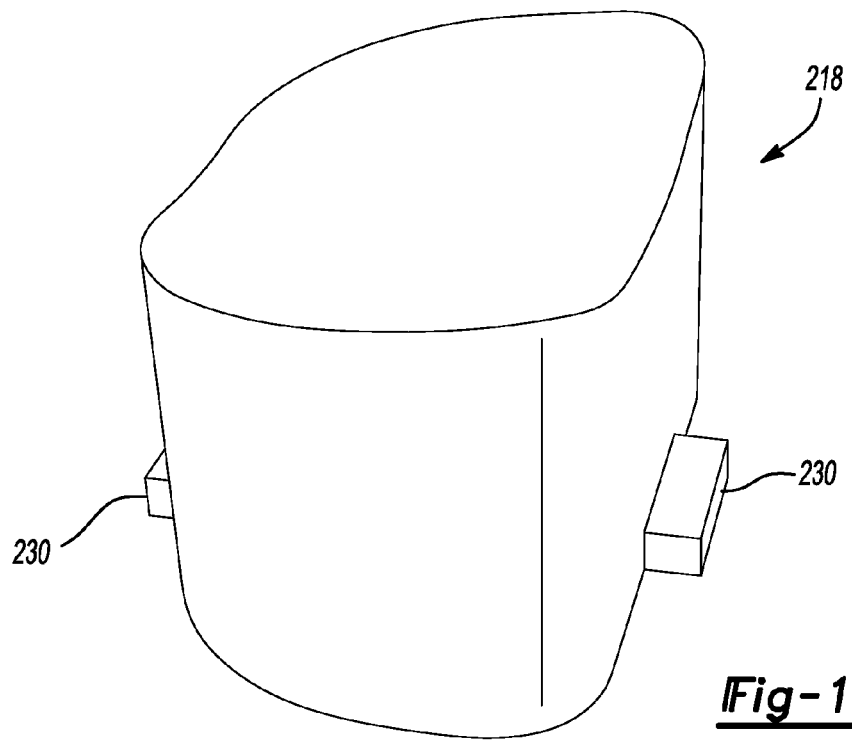
FIG. 12 is a perspective view of a mobile bearing that slidably cooperates within a pocket formed on the fixed bearing of FIG. 11.
Figure 13:
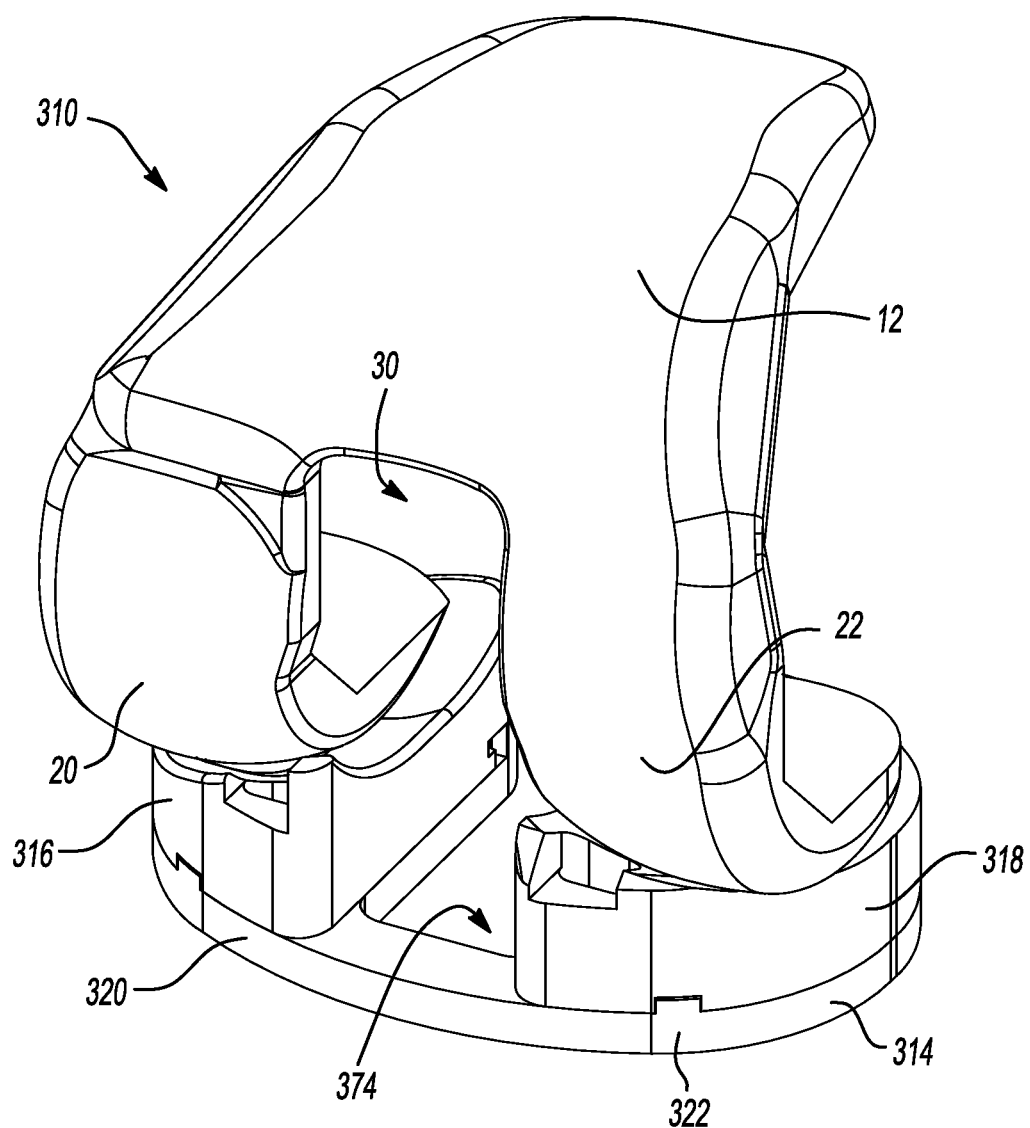
FIG. 13 is an anterior perspective view of a knee prosthesis assembly according to another example of the present teachings that incorporates a mobile bearing component that is selectively attachable to a medial side of a tibial tray and a fixed bearing component that is selectively attachable to a lateral side of the tibial tray.

While the embodiment shown in the figures includes a floating bearing provided on a medial side and a fixed bearing provided on a lateral side, the location of these bearings can be swapped. Similarly, both of the medial and lateral sides can be formed with floating bearings or fixed bearings. Turning now to FIGS. 9-11, a knee prosthesis assembly constructed in accordance to additional features of the present teachings is shown and generally identified at reference numeral 210. The knee prosthesis assembly 210 can generally include a femoral component 212, a tibial tray 214, a medial side having a mobile bearing component 216 and a lateral side having a fixed bearing 220. The mobile bearing component has a fixed portion 217 and a mobile bearing portion 218. The femoral component 212 can be constructed similar to the femoral component 12 described below. The fixed bearing 220 can be constructed similar to the lateral fixed bearing 18 described above. The mobile bearing component 216 can provide articulation that is fully conforming with the femoral component 212. The mobile bearing portion 218 can be captured around its perimeter by a pocket 222 formed by the fixed portion 217. In this way, the mobile bearing portion 218 can have a reduced likelihood of becoming dislocated relative to the fixed portion 217. While the mobile bearing component 216 is shown generally associated with the lateral side of the tibial tray 214, such a configuration can be additionally or alternatively provided on the medial portion of the tibial tray 214. In one example, the mobile bearing portion 218 can be formed by polyethylene or polyetheretherketone (PEEK). As shown in FIG. 11, the fixed portion 217 can have a pair of channels 226 formed thereon for guiding tabs 230 provided on the mobile bearing portion 218 (FIG. 12). It will be appreciated that while the mobile bearing component 216 has been described and shown incorporated on a medial portion of the tibial tray 214, it can additionally or alternatively be incorporated on a lateral portion of the tibial tray 214. Likewise, while the fixed bearing 220 has been described and shown incorporated on a lateral portion of the tibial tray 214, it can additionally or alternatively be incorporated on a medial portion of the tibial tray 214.

With reference now to FIGS. 13-16, a knee prosthesis assembly 310 constructed in accordance to additional features of the present teachings will be described. As with the other knee prosthesis assemblies disclosed herein, the knee prosthesis assembly 310 can be patient specific, such that each component can be constructed for optimal features for a given patient. In this regard, the knee prosthesis assembly 310 can generally include the femoral component 12, a tibial tray 314, a mobile bearing component 316 and a fixed bearing component 318. As shown, the mobile bearing component 316 is selectively secured to a medial portion 320 of the tibial tray 314 and a fixed bearing component 318 selectively secured to a lateral portion 322 of the tibial tray 314 for a left knee. However, it will be appreciated by those skilled in the art that a mobile bearing component 316 can be provided for both the medial portion 320 and the lateral portion 322 of the tibial tray 314. Similarly, a fixed bearing component 318 can be provided for both of the medial portion 320 and the lateral portion 322 of the tibial tray 314. Likewise, the fixed bearing component 318 can alternatively be provided only on the medial portion 320, while a mobile bearing component 316 can be provided only on a lateral portion 322 of the tibial tray 314. In sum, any combination of mobile and fixed bearing components can be available and selectively secured to either of the medial or lateral portions 320 and 322 of the tibial tray 314.

The femoral component 12 can be generally formed similar to the femoral component 12 described in detail above. Again, the medial condyle portion 20 can have a spherical, convex articulation surface that can cooperate with the mobile bearing components 316 as will be described herein. It is appreciated that a similar spherical, convex articulation surface can be provided on the lateral condyle portion 22 in the event that a mobile bearing component is desired on the lateral portion 322 of the tibial tray 314.

Figure 14:
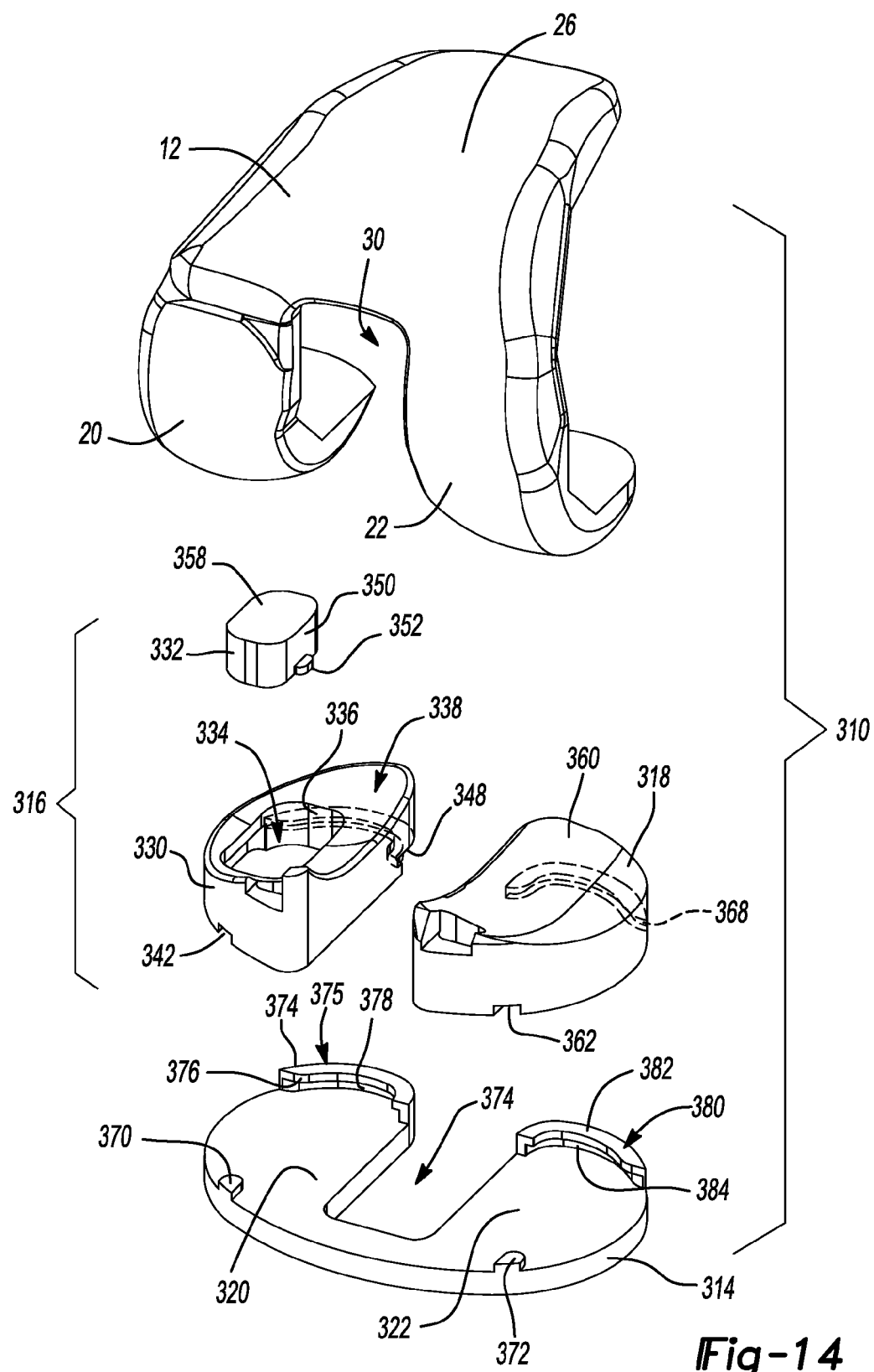
FIG. 14 is an anterior superior exploded perspective view of the knee prosthesis assembly of FIG. 13.
Figure 15:
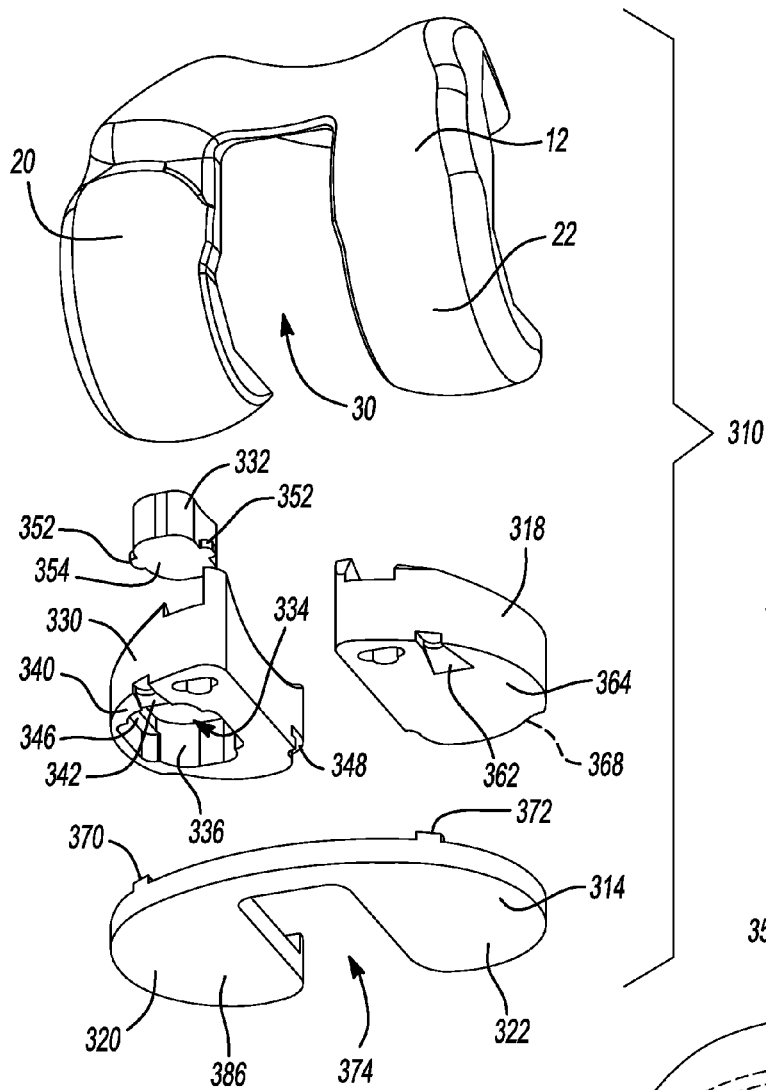
FIG. 15 is an anterior inferior exploded perspective view of the knee prosthesis assembly of FIG. 13.

The mobile bearing component 316 can generally include a fixed portion 330 and a mobile bearing portion 332 (FIG. 14). The fixed portion 330 can generally include a pocket 334 defined within a surrounding wall 336. A superior surface 338 can be contoured to cooperate with the profile of the medial condyle portion 20 of the femoral component 12. An inferior surface 340 (FIG. 15) can have a channel 342 that tapers generally anteriorly for locking with a portion of the tibial tray 314 as further discussed herein. A rail 346 can be formed into the surrounding wall 336. A groove 348 can be formed around a posterior edge of the fixed portion 330. The fixed portion 330 can have an inner wall 349 that cooperates with the U-shaped profile of the tibial tray 314 to accommodate a host or reconstructed ACL.

Figure 16:
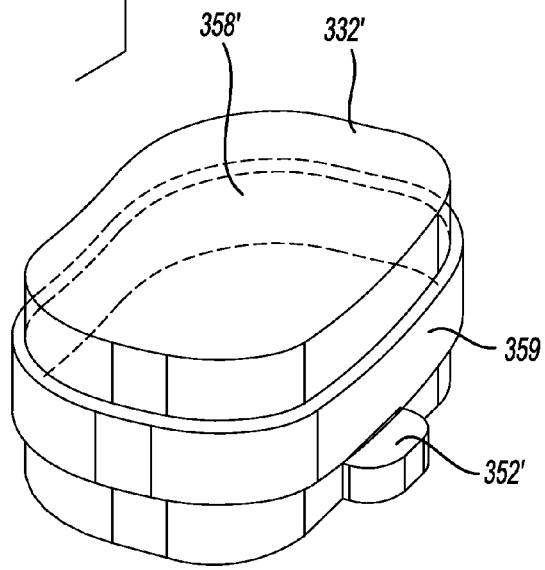
FIG. 16 is a perspective view of a mobile bearing incorporating a metal sleeve according to various features.

The mobile bearing portion 332 can have an outer perimeter surface 350 that substantially matches a profile of the surrounding wall 336, however, is reduced in size so as to be stepped inwardly relative to the surrounding wall 336 (see also FIG. 9) to allow movement within the surrounding wall 336. Tabs 352 can extend in generally the medial and lateral directions from an inferior surface 354 of the mobile bearing portion 332. A superior articulating surface 358 can substantially conform to the profile of the medial condyle portion 20 of the femoral component 12. The fixed portion 330 and the mobile bearing portion 332 can be formed of UHMWPE or PEEK. According to additional features, a mobile bearing portion 332' (FIG. 16) can have a metal layer or band 359 disposed around a perimeter. The metal layer 359 can preclude polymer-polymer contact between the perimeter of the mobile bearing portion 332' and the surrounding wall 336 of the fixed portion 330 to inhibit wear. As shown in FIG. 16, similar features are identified with common reference numerals having a "prime" suffix.

The fixed bearing component 318 can generally include a superior surface 360 that substantially conforms to and provides a surface contact with the profile of the lateral condyle portion 22 of the femoral component 12. A channel 362 can be formed along an anterior inferior surface 364 and that generally tapers anteriorly. A groove 368 can be formed around a posterior edge of the fixed bearing component 318. The fixed bearing component 318 can have an inner wall 369 that cooperates with the U-shaped profile of the tibial tray 314 to accommodate a host or reconstructed ACL.

The tibial tray 314 can generally include a locating tab 370 formed on an anterior edge of the medial portion 320 and a locating tab 372 formed on an anterior edge of the lateral portion 322. A slot 374 can be defined through the tibial tray 314 between the medial and lateral portions 320 and 322. The slot 374 can be configured to accommodate and provide clearance for a host ACL and/or PCL or a reconstructed ACL and/or PCL. A retaining rail 375 can be formed around a posterior edge of the medial portion 320. The retaining rail 375 can include a lip 376 and a groove 378. A retaining rail 380 can be formed around a posterior edge of the lateral portion 322 of the tibial tray 314. The retaining rail 380 can generally include a lip 382 and a groove 384. An inferior surface 386 of the tibial tray 314 can be generally smooth, but may also incorporate a series of round grooved pegs. The inferior surface 386 can be configured to be cemented or press-fit onto the proximal tibia. The tibial tray 314 can be generally manufactured of cobalt-chromium-molybdenum alloy or other suitable biocompatible materials.

Attaching the mobile bearing component 316 to the medial portion 320 of the tibial tray 314 will now be described according to one example. At the outset, the surgeon can select a given mobile bearing component 316 from a plurality of medial bearing components (see also kit 600, FIG. 21) that satisfies the desired characteristics for a given patient, such as height, articulation, etc. The mobile bearing portion 332 can be initially advanced into the pocket 334 superiorly, such that the tabs 352 can generally locate against the rail 346 formed on the fixed portion 330. Concurrently or subsequently, the fixed portion 330 can be located onto the medial portion 320 of the tibial tray 314 along with the mobile bearing portion 332 in an assembly. Next, a surgeon can slidably advance the mobile bearing component 316 in a directly generally posteriorly such that the channel 342 is progressively advanced around the locating tab 370 and the groove 348 of the fixed portion 330 is located under the lip 376 of the retaining rail 375 on the tibial tray 314. It will be appreciated that at this point, the fixed portion 330 remains static relative to the medial portion 320 of the tibial tray 314 while the mobile bearing portion 332 is free to slidably advance around the medial portion 320 of the tibial tray 314 within the confines of the surrounding wall 336 of the pocket 334. It can be appreciated that articulation of the medial condyle portion 20 of the femoral component on the superior articulating surface 358 of the mobile bearing portion 332 can influence the mobile bearing portion 332 to rotate and/or slidably advance such as in an anterior/posterior direction along the medial portion 320 around the pocket 334.

Connection of the fixed bearing component 318 to the lateral portion 322 of the tibial tray 314 is similarly carried out. Initially, the inferior surface 364 of the fixed bearing component 318 is located onto the lateral portion 322 of the tibial tray 314. Next, the fixed bearing component 318 is slidably advanced posteriorly, such that the channel 362 slidably accommodates the locating tab 372 while the groove 368 locates under the lip 382. The fixed bearing component 318 is adapted to be statically secured relative to the lateral portion 322 of the tibial tray when assembled.

Figure 17:
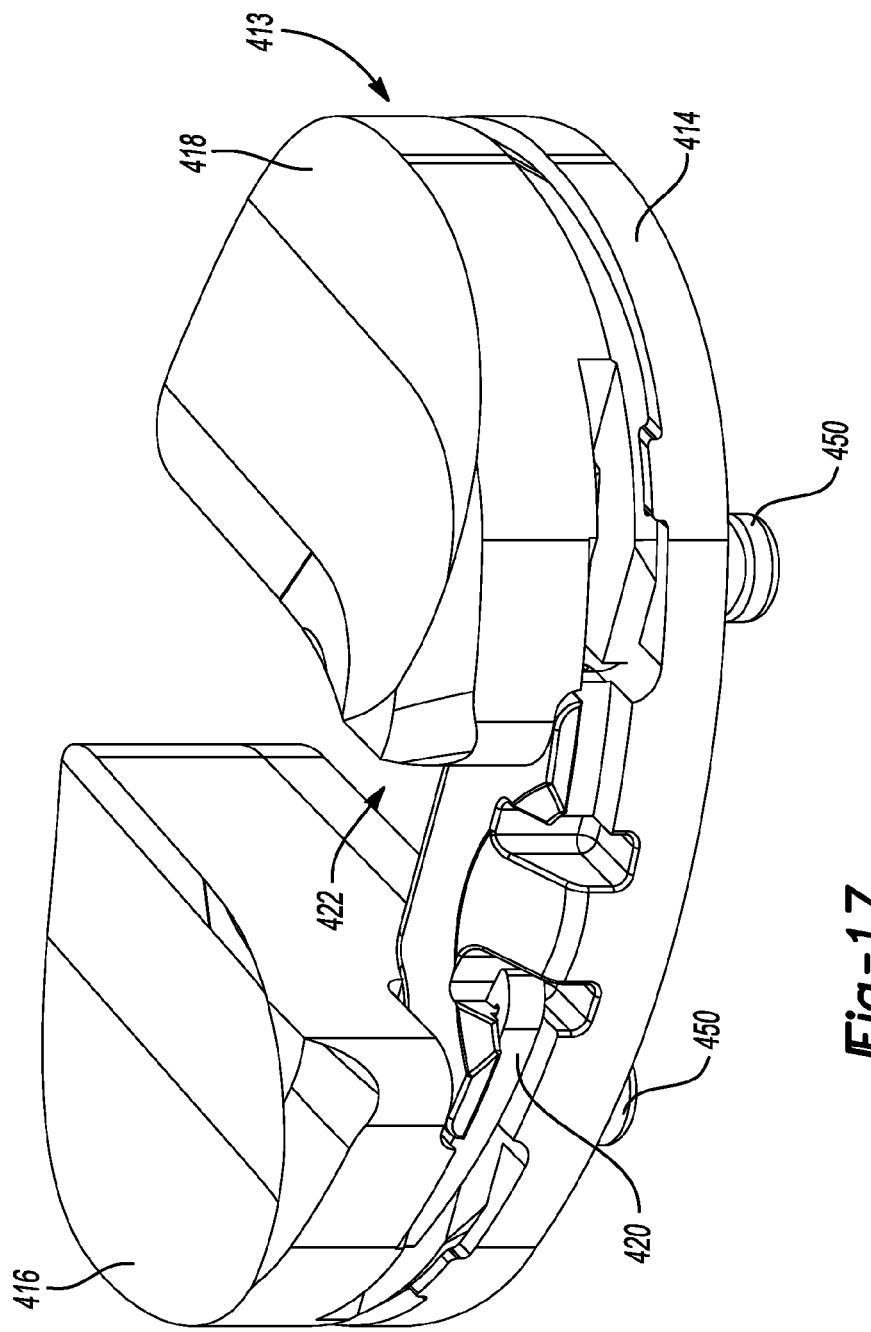
FIG. 17 is an anterior perspective view of a tibial tray constructed in accordance to additional features and incorporating a pair of fixed bearings that are selectively locked to the tibial tray with a locking bar.
Figure 18:
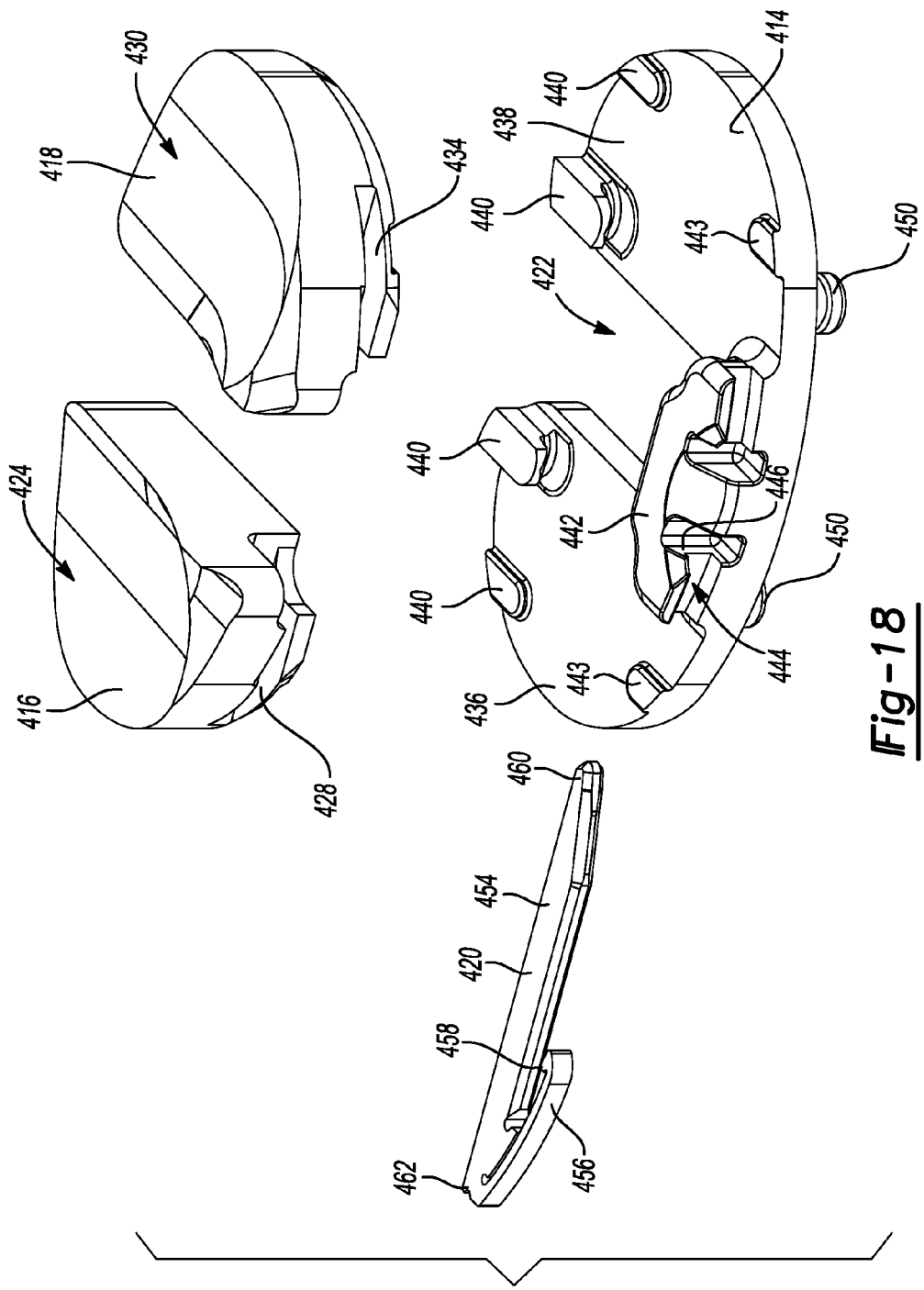
FIG. 18 is an anterior superior exploded perspective view of the tibial tray assembly of FIG. 17.
Figure 19:
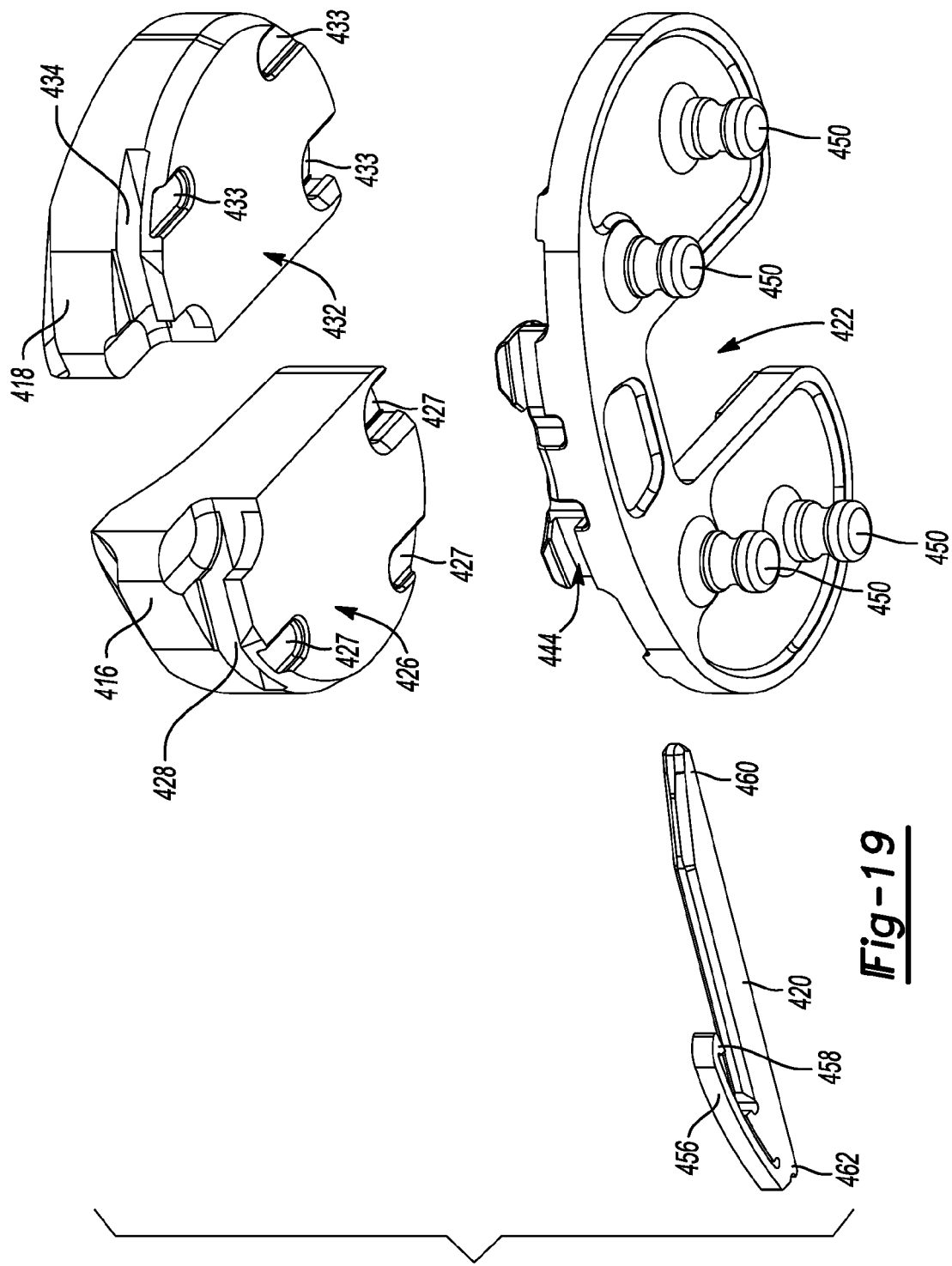
FIG. 19 is an anterior inferior exploded perspective view of the tibial tray assembly of FIG. 17.

With reference now to FIGS. 17-19, a tibial tray assembly 413 constructed in accordance to additional features of the present teachings will be described. As with the other knee prosthesis assemblies disclosed herein, the tibial tray assembly 413 can be patient specific, such that each component can be constructed for optimal features for a given patient. In this regard, the tibial tray assembly 413 can include a tibial tray 414, a first bearing component 416, a second bearing component 418 and a locking bar 420. As with the tibial tray 314 described above, the tibial tray 414 can be generally U-shaped and provides a slot 422 that can be configured to accommodate and provide clearance for a host ACL and/or PCL or a reconstructed ACL and/or PCL. Other examples of attaching an artificial or natural ACL and/or PCL may be found in "Knee Prosthesis Assembly with Ligament Link," U.S. Pat. No. 8,343,227 (issued Jan. 1, 2013) and U.S. Pat. No. 8,500,818 (issued aug. 6, 2013). As with the other bearing components disclosed herein, the first bearing component 416 and the second bearing component 418 are both independently formed and intraoperatively selected according to the needs of a given patient. The first bearing component 416 and the second bearing component 418 are generally fixed bearing components, however, a mobile bearing component may be similarly provided for either of the medial and/or lateral sides. As will become appreciated from the following discussion, the locking bar 420 can be used to selectively and intraoperatively secure the respective first and second bearing components 416 and 418 to the tibial tray 414. The first bearing component 416 can have a superior surface 424, an inferior surface 426 (FIG. 19) having engagement grooves 427 and an anterior channel 428. Similarly, the second bearing component 418 can include a superior surface 430, an inferior surface 432 (FIG. 19) having engagement grooves 433 and an anterior channel 434.

The tibial tray 414 can include a medial portion 436, a lateral portion 438, posterior engagement tabs 440, an anterior engagement bridge 442 and anterior engagement tabs 443. The anterior engagement bridge 442 can include a track 444 formed thereon. The anterior engagement bridge 442 can provide an increased thickness to the tibial tray 414 at the connection between the medial and lateral portion 436 and 438, respectively to increase durability. A wall 446 can be formed on the anterior engagement bridge 442 adjacent to the track 444. The tibial tray 414 can have inferiorly extending posts 450.

The locking bar 420 can generally include a body 454 having a finger 456 extending therefrom. A catch 458 can be formed on a terminal end of the finger 456. The locking bar 420 can be formed of biocompatible metallic material, such as titanium for example. The body 454 can further include a leading end 460 and a trailing end 462.

Attaching the respective first and second bearing components 416 and 418 to the tibial tray 414 according to one example of the present teachings will now be described. Once a surgeon has selected a first and second bearing component 416 and 418 that satisfies the given needs of a particular patient (see also kit 600, FIG. 21), they are independently located onto the medial and lateral portions 436 and 438 of the tibial tray 414. In this regard, the posterior engagement tabs 440 of the tibial tray 414 can locate into the respective engagement grooves 427 and 433 of the first and second bearing components 416 and 418. In some examples, the respective first and second bearing components 416 and 418 may be advanced posteriorly, such that the engagement tabs 440 can lock into the engagement grooves 427 and 433.

Concurrently, the anterior tabs 443 can locate into the anterior engagement grooves 427 and 433 of the first and second bearing components 416 and 418. Next, a surgeon can slidably advance the leading end 460 of the locking bar 420 through the respective anterior channels 428 and 434 of the first and second bearing components 416 and 418. Concurrently, a portion of the body 454 can locate along a posterior side of the anterior engagement bridge 442 while the finger 456 locates around an anterior side of the anterior engagement bridge 442. The locking bar 420 can be further advanced until the catch 458 on the finger 456 can locate around the wall 446 on the anterior engagement bridge 442.

Figure 20:
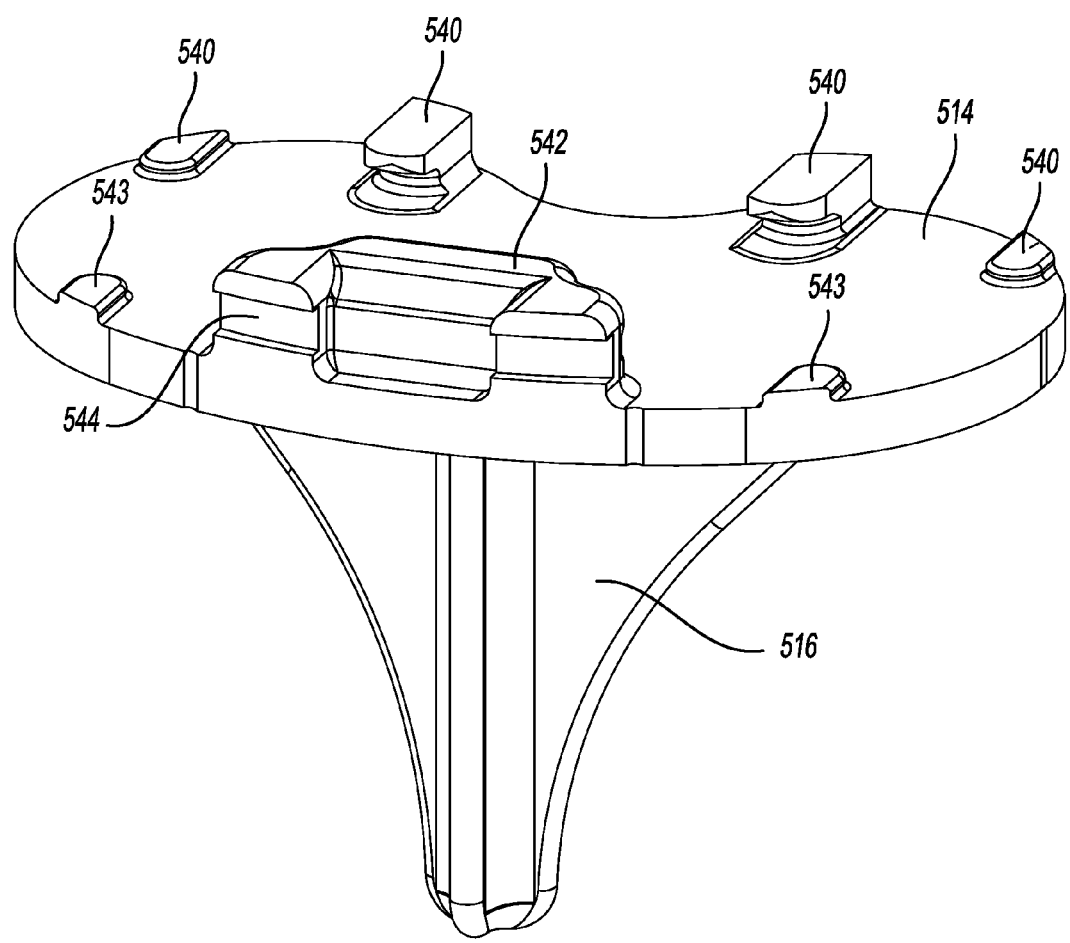
FIG. 20 is an anterior perspective view of a tibial tray constructed in accordance with additional features of the present teachings.

With reference now to FIG. 20, another tibial tray 514 constructed in accordance to the present teachings is shown. The tibial tray 514 generally includes an inferiorly extending stem 516. The tibial tray 514 can be a full tibial tray that can be particularly suited for examples where a central slot (such as the slot 422) for accommodating an ACL is not needed. The tibial tray 514 includes posterior engagement tabs 540 and an anterior engagement bridge 542. Anterior locating tabs 543 can be formed on the tray 514. The anterior engagement bridge 542 can include a track 544. The tibial tray 514 can be configured to selectively and intraoperatively secure independent medial and lateral bearings, such as the bearings 416 and 418 disclosed herein.

Figure 21:
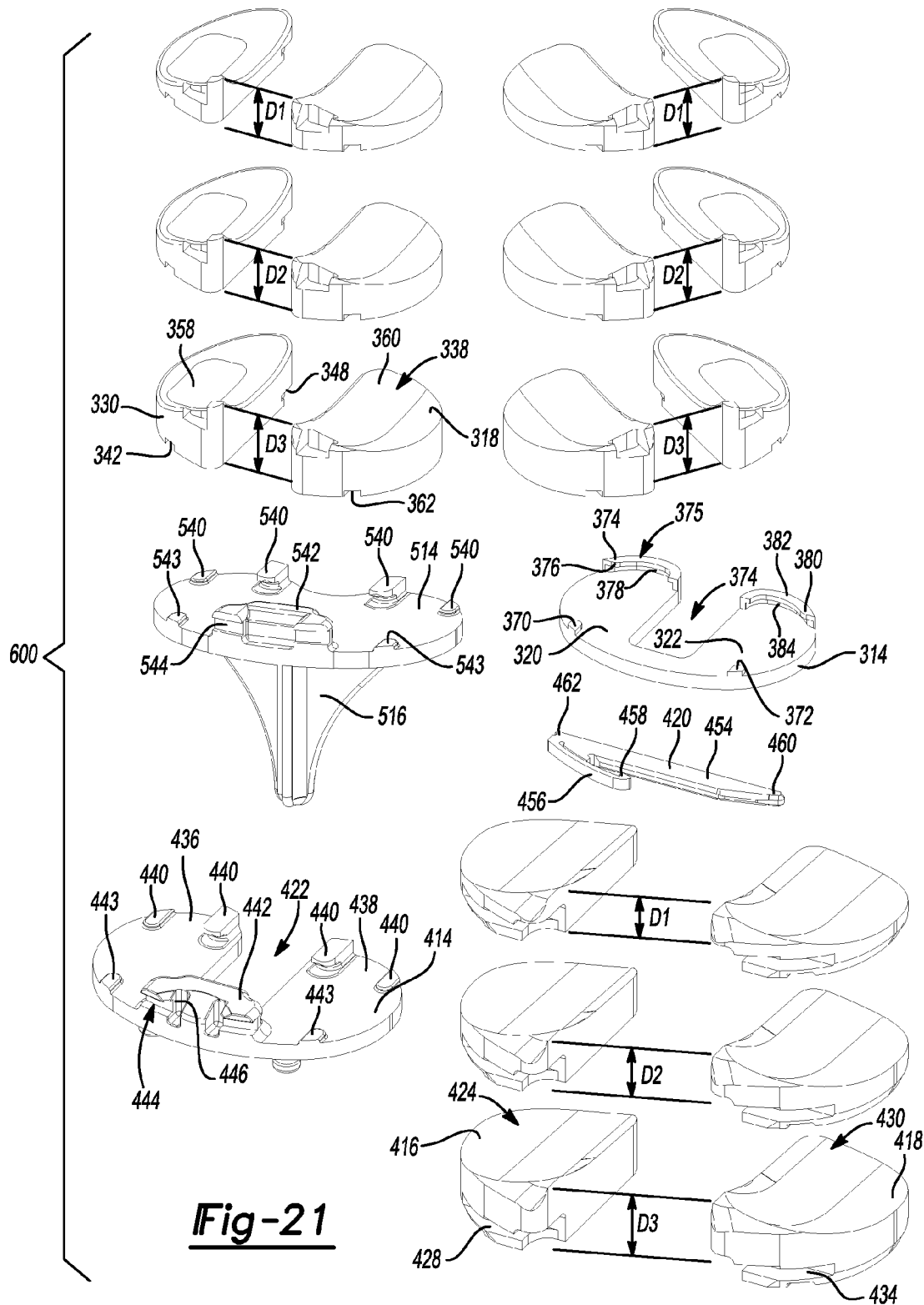
FIG. 21 is a kit having a plurality of tibial trays, medial bearings and lateral bearings according to the present teachings.

Turning now to FIG. 21, a kit 600 is shown having a collection of medial and lateral bearings that provide unique articulations, sizes and thicknesses (i.e., D1, D2, D3, etc.) and incorporate either a fixed or mobile configuration on the lateral and medial sides. The kit 600 further includes the bicruciate retaining tibial tray and the posterior cruciate retaining tray. As disclosed herein, the kit can be particularly suited for allowing a surgeon the opportunity to intraoperatively select a given medial and/or lateral bearing component and tibial tray that is particularly suited for a given patient. It is contemplated that with the kit 600, a surgeon can also utilize the components during a revision surgery where the level of constraint needs to be increased. In this regard, a surgeon may only desire to change some components while leaving others unchanged.

As used herein, the terms superior, superiorly, superior direction are used to generally refer to the anatomical meaning, such as higher in place or position or generally situated above. Similarly, the terms inferior, inferiorly, inferior direction are used to generally refer to the anatomical meaning, such as lower in place or position or generally situated below.

Figure 22:
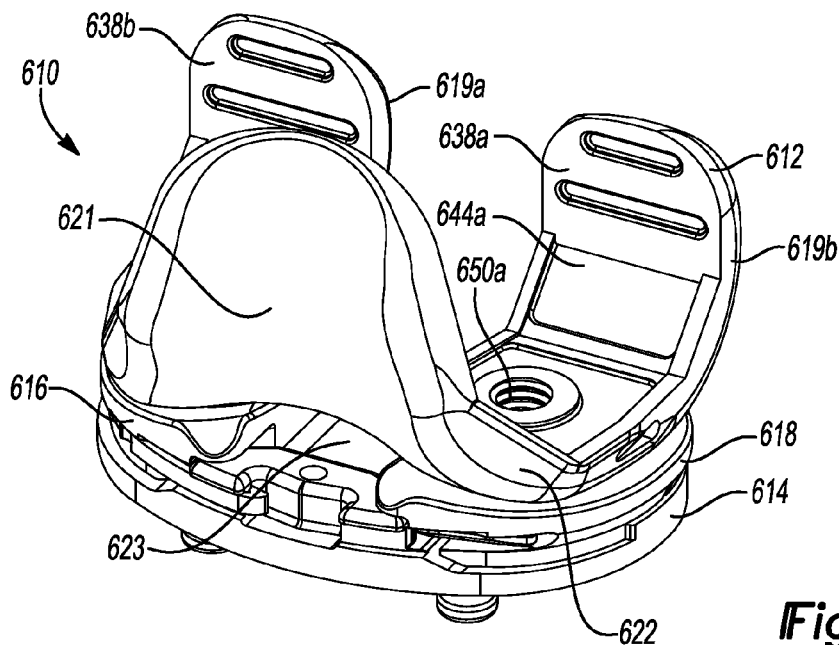
FIG. 22 is an anterior perspective view of a knee prosthesis constructed in accordance to additional features of the present teachings.
Figure 23:
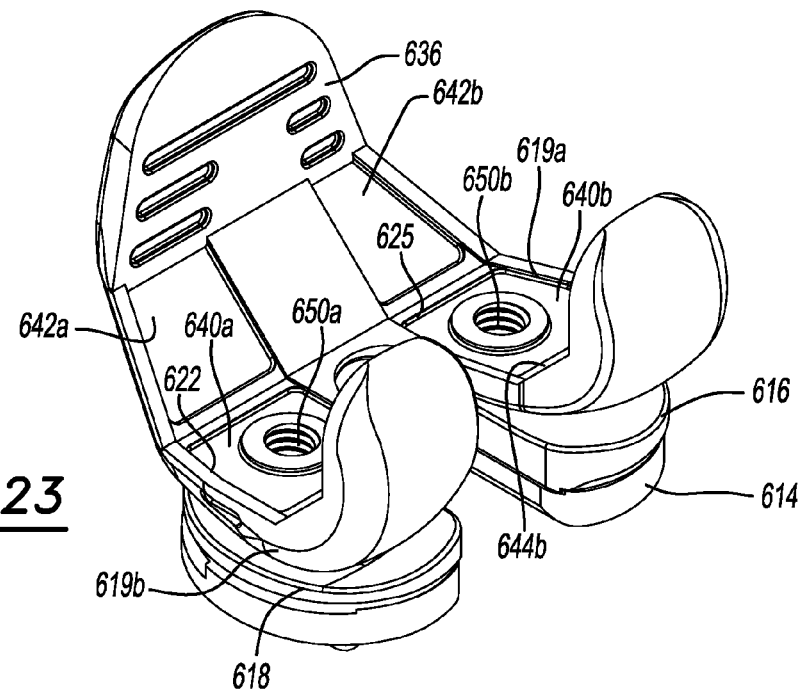
FIG. 23 is a posterior perspective view of the knee prosthesis of FIG. 22.

Turning now to FIGS. 22 and 23, a knee prosthesis assembly constructed in accordance to another example of the present teachings is shown and generally identified at reference numeral 610. The knee prosthesis assembly 610 can generally include a femoral component 612, a tibial tray 614, a medial or first fixed bearing 616 and a lateral or second fixed bearing 618. Similar to the other knee prosthesis assemblies disclosed herein, the knee prosthesis assembly 610 can be used when it is desirable to retain or reconstruct an ACL or PCL.

The respective components of the knee prosthesis assembly 610 can be patient specific, such that each component can be constructed for optimal features for a given patient. For example, the bone interface margins of the femoral component 612 and tibial tray 614 can be patient specific for optimized bone coverage. In addition, the overall size, such as anterior-posterior dimensions and bone cut geometry can be determined and used for manufacturing the components of the knee prosthesis assembly 610. Moreover, some articulation features can be determined and used as criteria for forming the components of the knee prosthesis assembly 610. In sum, each of the components of the knee prosthesis assembly 610 can be a patient-specific implant, a semi-custom implant or an off-the-shelf or standard production implant. A custom-made implant is a patient-specific, one-of-a-kind implant specifically made for a particular patient, and consequently there is no excess inventory associated with multiple sizes of implants. Other configurations are contemplated.

The femoral component 612 will now be described in greater detail. The femoral component 612 can generally comprise a cruciate retaining prosthesis and includes various portions to replace or mimic the distal femur. The femoral component 612 can include a medial condyle portion 619a and a lateral condyle portion 619b. The condyle portions 619a and 619b can replace the medial and lateral condyles of a distal femur. The medial and lateral condyle portions 619a and 619b can interconnect and be formed as a single piece with a patellar track portion 621. The patellar track portion 621 can allow for articulation of a patella, either natural or prosthetic patella, once the femoral component 612 is implanted into the distal femur. The medial and lateral condyle portions 619a and 619b and the patellar track portion 621 can generally define an exterior portion of the femoral component 612. The femoral component 612 can define an opening or passage 623 between the medial and lateral condyle portions 619a and 619b. As can be appreciated, the passage 623 can accommodate, and provide clearance for a host ACL and/or PCL or a reconstructed ACL and/or PCL.

The femoral component 612 can include a bone contacting or inferior surface 625 (FIG. 23). The inferior surface 625 can include an anterior surface 636 that can be substantially flat and formed generally parallel to a pair of posterior surfaces 638a and 638b. A pair of intermediate surfaces 640a and 640b are provided generally at an intermediate portion of the inferior surface 625. A pair of angled anterior transition surfaces 642a and 642b generally connect the anterior surface 636 with the intermediate surfaces 640a and 640b. Similarly, a pair of angled posterior transition surfaces 644a and 644b are provided between the respective posterior surfaces 638a and 638b and the intermediate surfaces 640a and 640b. In one example, a threaded boss 650a and 650b can be provided on each of the intermediate surfaces 640a and 640b, respectively. The bosses 650a and 650b can be optionally used to threadably couple with various augments (not specifically shown) as necessary. The femoral component 612 can be formed as a unitary structure and cast of a biocompatible high strength alloy, such as cobalt-chromium-molybdenum alloy or similar suitable material. All surfaces, which do not contact the femur, can be highly polished to provide smooth articulating bearing surfaces. The interior surface 625 of the femoral component 612 can be roughened or uneven or include porous material to allow bone ingrowth or attachment with bone cement.

Figure 24:
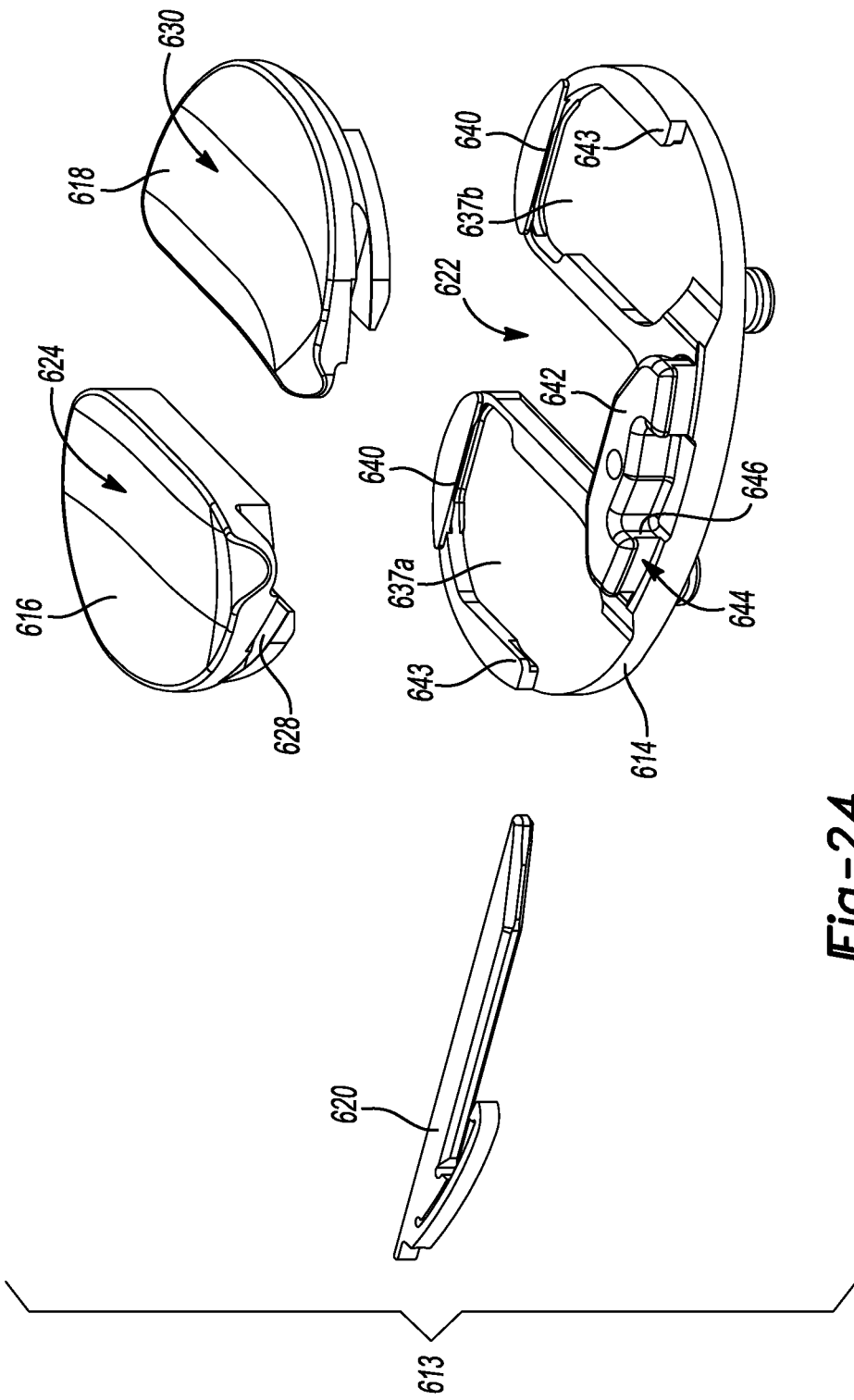
FIG. 24 is an anterior superior exploded perspective view of a tibial tray assembly of the knee prosthesis of FIG. 22.
Figure 25:
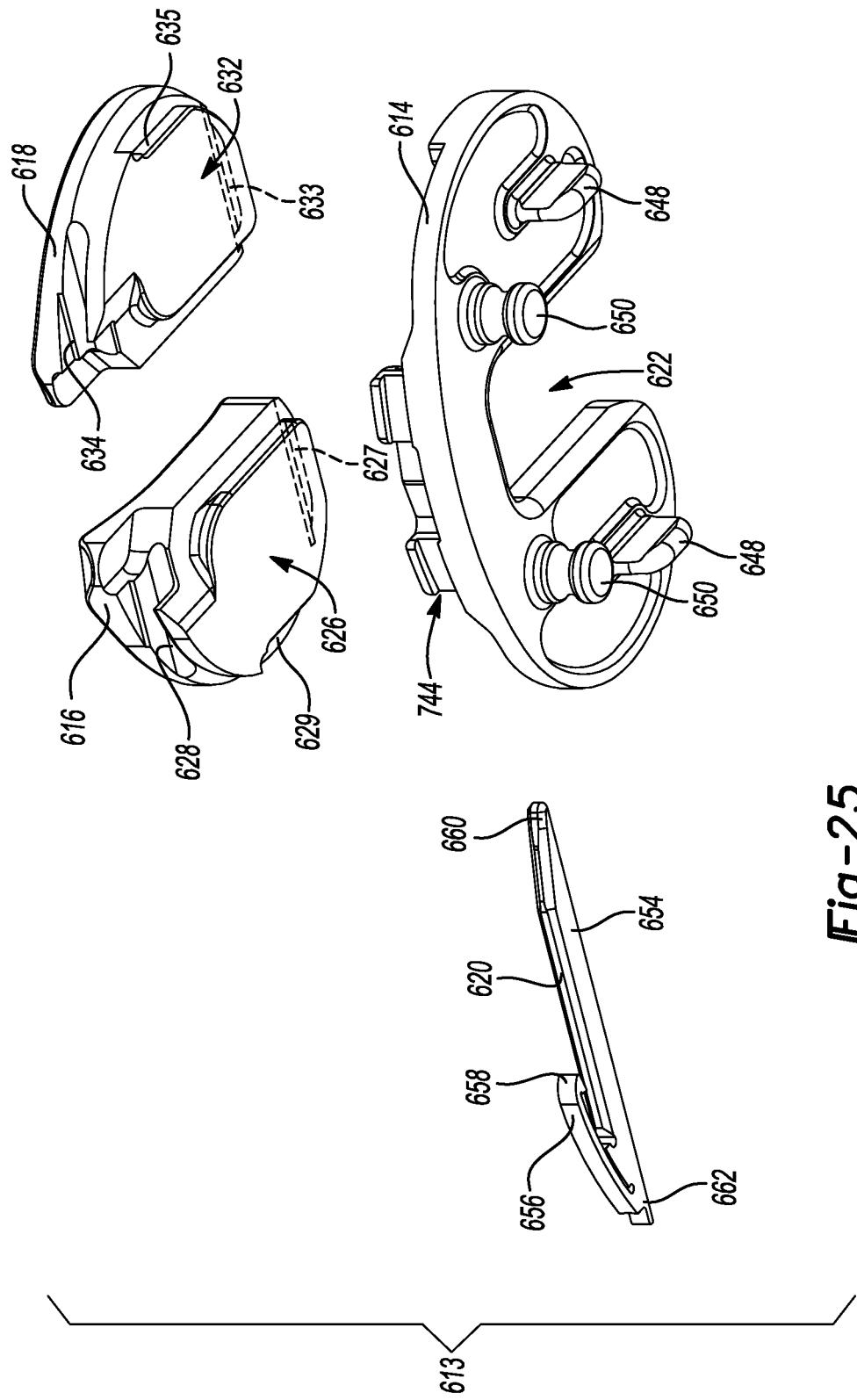
FIG. 25 is an anterior inferior exploded perspective view of the tibial tray assembly of FIG. 24.

With reference now to FIGS. 24 and 25, a tibial tray assembly 613 constructed in accordance to the present disclosure will be described. As with the other knee prosthesis assemblies disclosed herein, the tibial tray assembly 613 can be patient specific, such that each component can be constructed for optimal features for a given patient. In this regard, the tibial tray assembly 613 can include the tibial tray 614, the first bearing component 616, the second bearing component 618, and a locking bar 620. The tibial tray 614 can be generally U-shaped and provides a slot 622 that can be configured to accommodate and provide clearance for a host ACL and/or PCL or a reconstructed ACL and/or PCL. As with the other bearing components disclosed herein, the first bearing component 616 and the second bearing component 618 are both independently formed and intraoperatively selected according to the needs of a given patient. The first bearing component 616 and the second bearing component 618 are generally fixed bearing components. The locking bar 620 can be used to selectively and intraoperatively secure the respective first and second bearing components 616 and 618 to the tibial tray 614. The first bearing component 616 can have a superior surface 624, an inferior surface 626 (FIG. 25) having a posterior groove 627, an anterior channel 628 and an outer groove 629. Similarly, the second bearing component 618 can include a superior surface 630, an inferior surface 632 (FIG. 25) having a posterior groove 633, an anterior channel 634 and an outer groove 635.

The tibial tray 614 can include a medial portion 637a, a lateral portion 637b, posterior engagement lips 640, an anterior engagement bridge 642, and outer securing lips 643. The anterior engagement bridge 642 can include a track 644 formed thereon. The anterior engagement bridge 642 can provide an increased thickness to the tibial tray 614 at the connection between the medial and lateral portions 637a and 637b, respectively to increase durability. The tibial tray 614 can have inferiorly extending keels 648 and inferiorly extending posts 650.

The locking bar 620 can generally include a body 654 having a finger 656 extending therefrom. A catch 658 can be formed on a terminal end of the finger 656. The locking bar 620 can be formed of biocompatible metallic material, such as titanium for example. The body 654 can further include a leading end 660 and a trailing end 662.

Attaching the respective first and second bearing components 616 and 618 to the tibial tray 614 according to one example of the present teachings will be described. Once a surgeon has selected a first and second bearing components 616 and 618 (such as from a kit 700, FIG. 28) that satisfies the given needs of a particular patient, they are independently located onto the medial and lateral portions 637a and 637b of the tibial tray 614. In this regard, the posterior engagement lips 640 of the tibial tray 614 can locate into the respective posterior engagement grooves 627 and 633 of the first and second bearing components 616 and 618. In some examples, the first and second bearing components 616 and 618 can be initially located against the superior surface of the tibial tray 614 and slidably advanced posteriorly until the posterior engagement lips 640 can lock into the engagement grooves 627 and 633. Concurrently, the outer securing lips 643 can locate into the corresponding outer grooves 629 and 635 of the respective first and second bearing components 616 and 618. Next, a surgeon can slidably advance the leading end 660 of the locking bar 620 through the respective anterior channels 628 and 634 of the first and second bearing components 616 and 618. Concurrently, a portion of the body 654 can locate along a posterior side of the anterior engagement bridge 642 while the finger 656 locates around an anterior side of the anterior engagement bridge 642. The locking bar 620 can be further advanced until the catch 658 on the finger 656 can locate around the wall 646 on the anterior engagement bridge 642.

Figure 26:
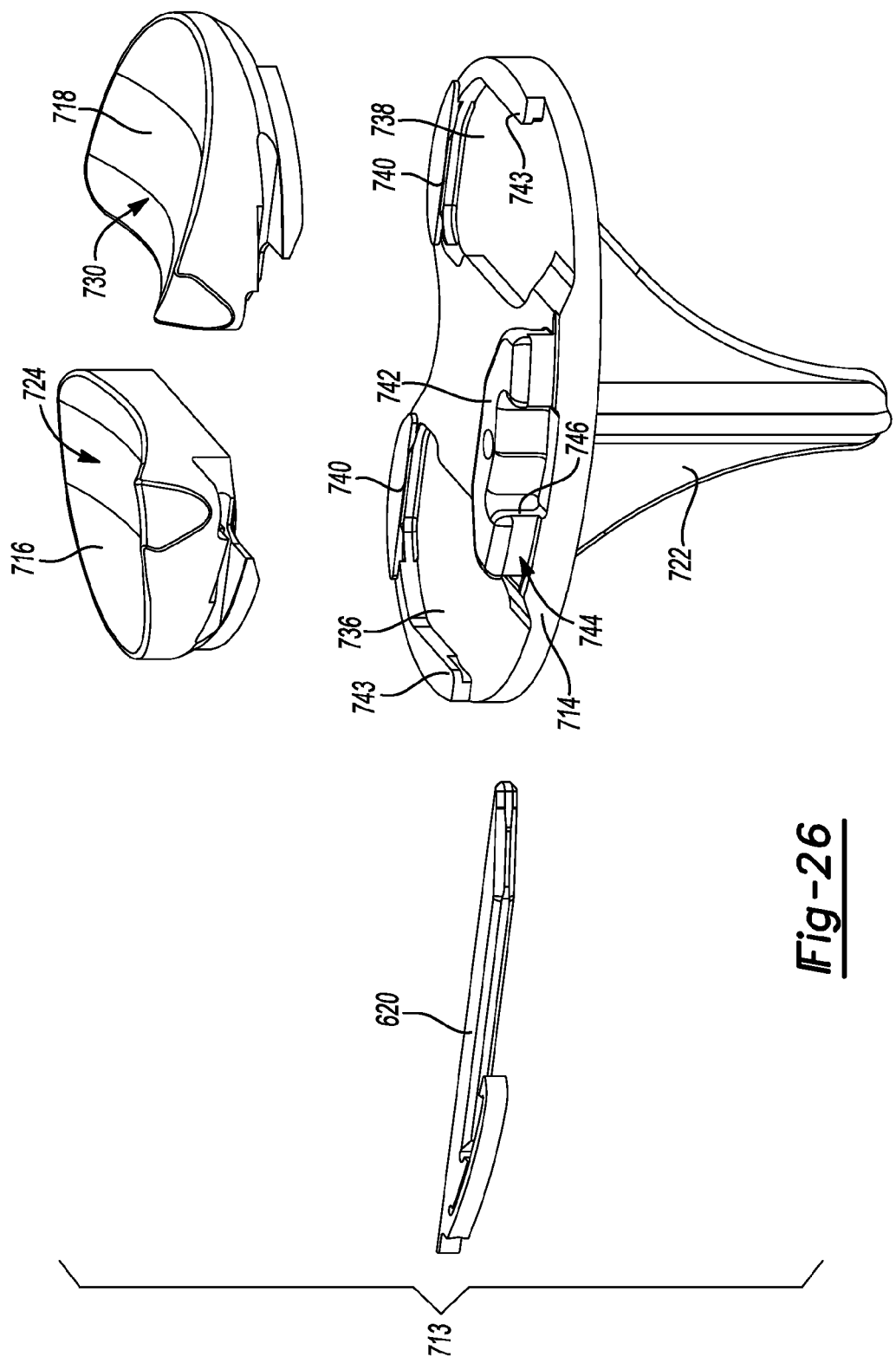
FIG. 26 is an anterior superior exploded perspective view of a tibial tray assembly constructed in accordance to additional features.
Figure 27:
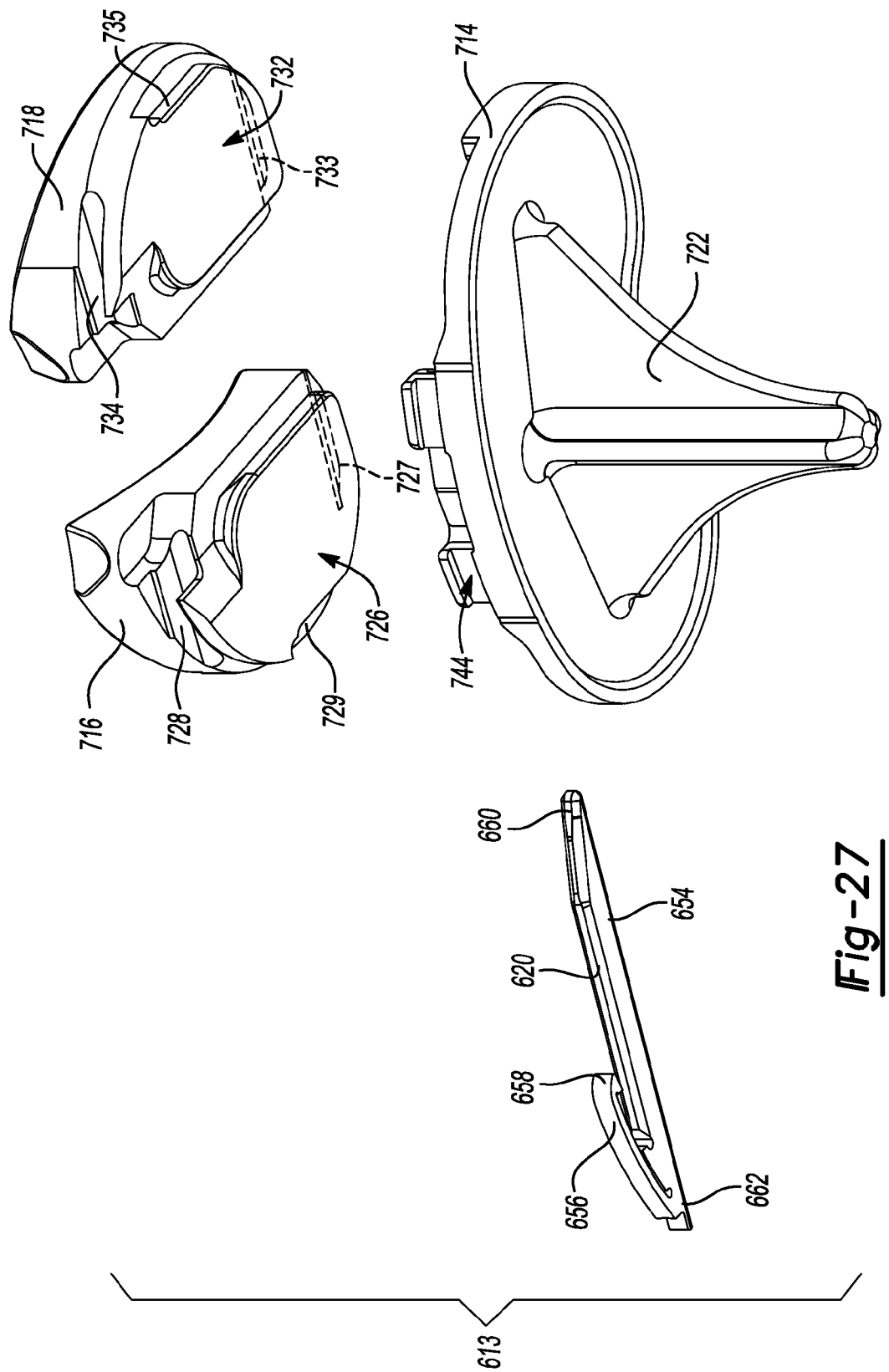
FIG. 27 is an anterior inferior perspective view of the tibial tray assembly of FIG. 26.

With reference now to FIGS. 26 and 27, a tibial tray assembly 713 constructed in accordance to the present disclosure will be described. As with the other knee prosthesis assemblies disclosed herein, the tibial tray assembly 713 can be patient specific, such that each component can be constructed for optimal features for a given patient. In this regard, the tibial tray assembly 713 can include a tibial tray 714, a first bearing component 716, a second bearing component 718, and the locking bar 620. The tibial tray 714 may be configured for use with other femoral components not specific to cruciate retaining. The tibial tray 714 can have an inferiorly extending stem 722. As with the other bearing components described herein, the first bearing component 716 and the second bearing component 718 are both independently formed and intraoperatively selected according to the needs of a given patient. The first bearing component 716 and the second bearing component 718 are generally fixed bearing components. The locking bar 620 can be used to selectively and intraoperatively secure the first and second bearing components 716 and 718 to the tibial tray 714. The first bearing component 716 can have a superior surface 724, an inferior surface 726 (FIG. 27) having a posterior groove 727, an anterior channel 728, and an outer groove 729. Similarly, the second bearing component 718 can have a superior surface 730, an inferior surface 732 (FIG. 27) having a posterior groove 733, an anterior channel 734, and an outer groove 735.

The tibial tray 714 can include a medial portion 736, a lateral portion 738, posterior engagement lips 740, an anterior engagement bridge 742, and outer securing lips 743. The anterior engagement bridge 742 can include a track 744 formed thereon. The anterior engagement bridge 742 can provide an increased thickness to the tibial tray 714 at the connection between the medial and lateral portions 736 and 738, respectively to increase durability.

Attaching the respective first and second bearing components 716 and 718 to the tibial tray 714 according to one example of the present teachings will be described. Once a surgeon has selected a first and second bearing components 716 and 718 (such as from the kit 700, FIG. 28) that satisfies the given needs of a particular patient, they are independently located onto the medial and lateral portions 736 and 738 of the tibial tray 714. In this regard, the posterior engagement lips 740 of the tibial tray can locate into the respective posterior engagement grooves 727 and 733 of the first and second bearing components 716 and 718. In some examples, the first and second bearing components 716 and 718 can be initially located against the superior surface of the tibial tray 714 and slidably advanced posteriorly until the posterior engagement lips 740 can lock into the respective grooves 727 and 733. Concurrently, the outer securing lips 743 can locate into the corresponding outer grooves 729 and 735 of the respective first and second bearing components 716 and 718. Next, a surgeon can slidably advance the leading end 660 of the locking bar 620 through the respective anterior channels 728 and 734 of the first and second bearing components 716 and 718. Concurrently, a portion of the body 654 can locate along a posterior side of the anterior engagement bridge 742 while the fingers 656 locates around the anterior side of the anterior engagement bridge 742. The locking bar 620 can be further advanced until the catch 658 on the fingers 656 can locate around the wall 746 on the anterior engagement bridge 742.

Figure 28:
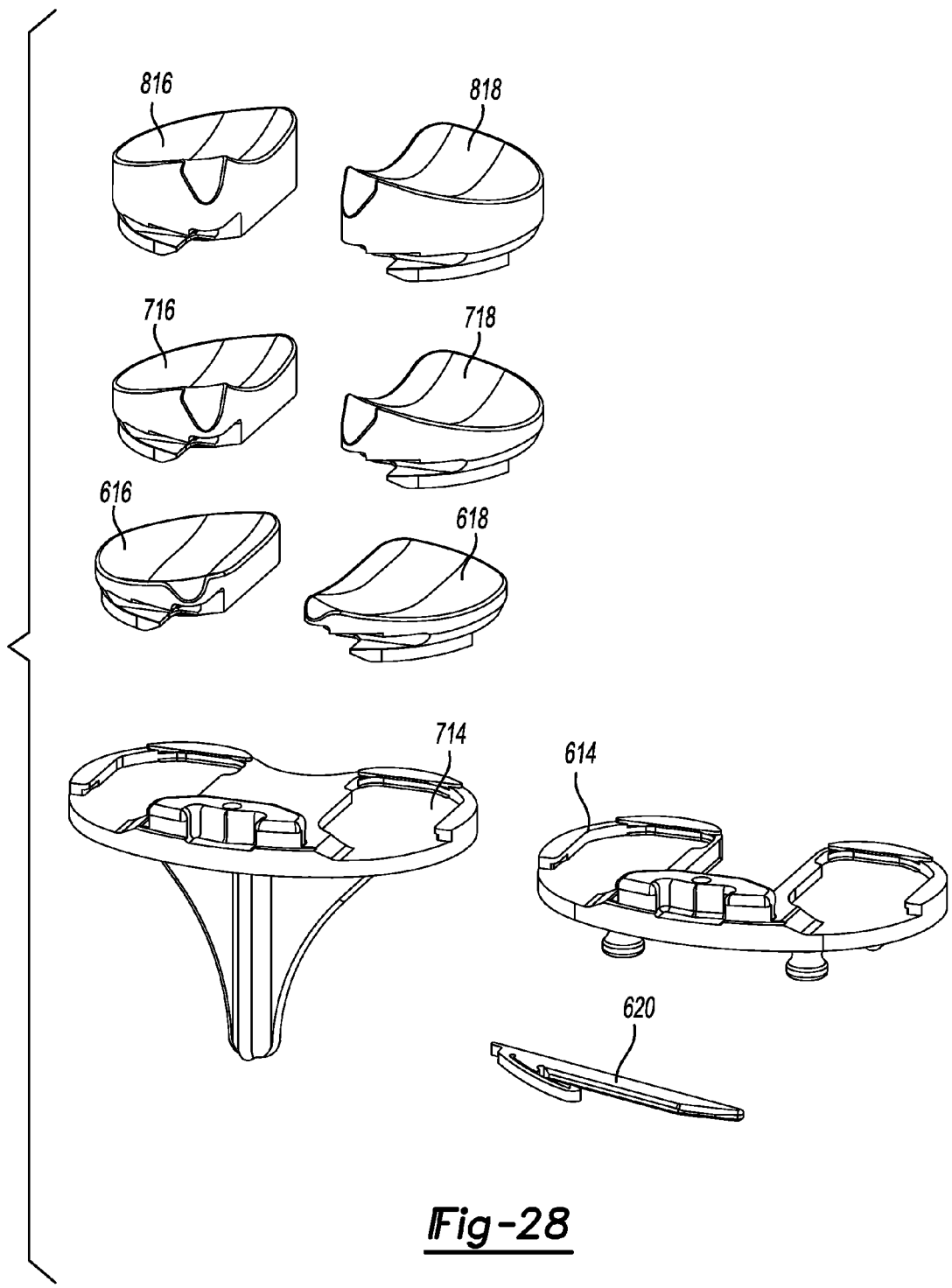
FIG. 28 is a kit having a plurality of tibial trays, medial bearings, and lateral bearings according to the present teachings.

Turning now to FIG. 28, a kit is shown that includes the tibial trays 614 and 714 as well as the locking bar 620, and a collection of bearing components including the first bearing components 616 and 716 as well as the second bearing components 618 and 718. A third set of bearing components including a first bearing component 816 and 818 may also be provided. In this regard, the respective bearings can provide various thicknesses and/or articulations that may be available in order to satisfy the needs of a particular patient.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A knee joint prosthesis assembly comprising:
   a femoral component having a medial and a lateral condyle portion connected by a patellar track portion, the femoral component forming an opening between the medial and lateral condyles;
   a unitary tibial component having a medial portion that includes a first posterior engagement lip and a first outer securing lip extending superiorly from a base surface at a medial end of the unitary tibial component, and a lateral portion that includes a second posterior engagement lip and a second outer securing lip extending superiorly from the base surface at a lateral end of the unitary tibial component, the first and the second outer securing lips are posterior to an anterior edge of the unitary tibial component, the first and the second posterior engagement lips are separate and spaced apart from one another and extend superiorly from the base surface;
   a medial bearing configured to be slid into cooperation with the medial portion of the unitary tibial component such that a first posterior groove formed on the medial bearing slidably engages the first posterior engagement lip and a first outer groove formed on the medial bearing at a medial side thereof slidably engages the first outer securing lip;
   a lateral bearing separately formed and independent from the medial bearing and configured to be slid into cooperation with the lateral portion of the unitary tibial component such that a second posterior groove formed on the lateral bearing slidably engages the second posterior engagement lip and a second outer groove formed on the lateral bearing at a lateral side thereof slidably engages the second outer securing lip; and
   a locking bar configured to couple with a track of an anterior engagement bridge extending from a superior surface of the unitary tibial component between the medial and lateral portions thereof, and configured to couple with the medial and lateral bearings to secure the medial and lateral bearings to the tibial component.

2. The knee joint prosthesis of claim 1 wherein the tibial component comprises a first peg extending inferiorly from the medial portion and a second peg extending inferiorly from the lateral portion.

3. The knee joint prosthesis of claim 2 wherein the tibial component further comprises a first keel extending inferiorly from the medial portion and a second keel extending inferiorly from the lateral portion.

4. The knee joint prosthesis of claim 2 wherein the medial and lateral bearings are both configured to be fixed relative to the tibial component.

5. The knee joint prosthesis of claim 1 wherein the medial and lateral condyles of the femoral component are configured to articulate along complementary bearing surfaces of the medial and lateral bearings.

6. The knee joint prosthesis of claim 1 wherein the tibial component is U-shaped and is adapted to accommodate an anterior cruciate ligament.

7. The knee joint prosthesis of claim 1 wherein the tibial component has an inferiorly extending stem.

8. The knee joint prosthesis of claim 1, further comprising a plurality of separate fixed medial and lateral bearings, wherein the plurality of medial and lateral bearings have distinct thicknesses in a superior/inferior direction.

9. A knee joint prosthesis assembly comprising:
a femoral component having a medial and a lateral condyle portion connected by a patellar track portion, the femoral component forming an opening between the medial and lateral condyles;
a unitary tibial component having a medial portion that includes a first pair of distinct and spaced apart engagement lips, a lateral portion that includes a second pair of distinct and spaced apart engagement lips, and an anterior engagement bridge between the medial portion and the lateral portion;
a medial bearing having a first pair of distinct and spaced apart grooves formed thereon that selectively slidably engage the first pair of engagement lips;
a lateral bearing separately formed and independent from the medial bearing and having a second pair of distinct and spaced apart grooves formed thereon that selectively slidably engage the second pair of engagement lips; and
a locking bar configured to couple with each one of the medial bearing, the lateral bearing, and the anterior engagement bridge to secure the medial and lateral bearings to the tibial component;
wherein:
the tibial component comprises a first peg extending inferiorly from the medial portion and a second peg extending inferiorly from the lateral portion;
the first pair of distinct and spaced apart engagement lips include a medial securing lip extending superiorly from a base surface of the unitary tibial component at a medial end of the unitary tibial component, and a medial posterior engagement lip extending superiorly from the base surface at a posterior end thereof;
the second pair of distinct and spaced apart engagement lips include a lateral securing lip extending superiorly from the base surface at a lateral end of the unitary tibial component, and a lateral posterior engagement lip extending superiorly from the base surface at the posterior end thereof, the medial and lateral posterior engagement lips are separate and spaced apart from one another;
the medial bearing is configured to slidably engage, in the anterior to posterior direction, the medial portion of the unitary tibial component;
the lateral bearing is configured to slidably engage, in the anterior to posterior direction, the lateral portion of the unitary tibial component; and
the medial and lateral bearings are both configured to be fixed relative to the tibial component.

10. The knee joint prosthesis of claim 9 wherein the tibial component further comprises a first keel extending inferiorly from the medial portion and a second keel extending inferiorly from the lateral portion.

11. The knee joint prosthesis of claim 9 wherein the medial and lateral condyles of the femoral component are configured to articulate along complementary bearing surfaces of the medial and lateral bearings.

12. The knee joint prosthesis of claim 9 wherein the tibial component is U-shaped and is adapted to accommodate an anterior cruciate ligament.

13. The knee joint prosthesis of claim 9 wherein the tibial component has an inferiorly extending stem.

14. The knee joint prosthesis of claim 9, further comprising a plurality of separate fixed medial and lateral bearings, wherein the plurality of medial and lateral bearings have distinct thicknesses in a superior/inferior direction.

15. The knee joint prosthesis of claim 9 wherein the first pair of engagement lips extend in different directions.

16. The knee joint prosthesis of claim 15 wherein the second pair of engagement lips extend in different directions.

17. A knee joint prosthesis assembly comprising:
a femoral component including medial and lateral condyle portions connected by a patellar track portion, the femoral component defining an opening between the medial and the lateral condyle portions;
a unitary tibial component including:
a medial base surface and a lateral base surface spaced apart from the medial base surface;
a medial engagement lip at a medial end of the medial base surface extending superiorly from the medial base surface, and a lateral engagement lip at a lateral end of the lateral base surface extending superiorly from the lateral base surface, both of the medial and the lateral engagement lips are posterior to an anterior edge of the unitary tibial component; and
a medial posterior lip at a medial posterior end of the medial base surface extending superiorly from the medial base surface, and a lateral posterior lip at a lateral posterior end of the lateral base surface extending superiorly from the lateral base surface, the medial and the lateral posterior lips are separate and spaced apart from one another;
an anterior engagement bridge between the medial and the lateral base surfaces;
a medial bearing defining a medial posterior groove configured to slidably couple with the medial posterior lip, and defining an outer medial groove configured to slidably couple with the medial engagement lip;
a lateral bearing defining a lateral posterior groove configured to slidably couple with the lateral posterior lip, and defining an outer lateral groove configured to slidably couple with the lateral engagement lip; and
a locking bar configured to couple with each one of the medial bearing, the lateral bearing, and the anterior engagement bridge to secure the medial and the lateral bearings to the unitary tibial component.

* * * * *

UNITED STATES PATENT AND TRADEMARK OFFICE
CERTIFICATE OF CORRECTION

| | |
|---|---|
| PATENT NO. | : 8,894,715 B2 |
| APPLICATION NO. | : 13/609389 |
| DATED | : November 25, 2014 |
| INVENTOR(S) | : Metzger |

Page 1 of 1

It is certified that error appears in the above-identified patent and that said Letters Patent is hereby corrected as shown below:

Title Page, Item (12) delete "Metzger et al." and insert -- Metzger --.

Title Page, Item (75) Inventors should read:

-- (75)   Inventor:   Robert Metzger, Wakarusa, IN (US) --.

Signed and Sealed this
Seventh Day of April, 2015

Michelle K. Lee
*Director of the United States Patent and Trademark Office*